US006280742B1

(12) United States Patent
Seid et al.

(10) Patent No.: US 6,280,742 B1
(45) Date of Patent: Aug. 28, 2001

(54) METHODS AND MATERIALS FOR THE TREATMENT OF PROSTATIC CARCINOMA

(75) Inventors: Christopher Allen Seid, The Woodlands; Gurpreet Singh, Houston, both of TX (US)

(73) Assignee: Zonagen, Inc., The Woodlands, TX (US)

( * ) Notice: Subject to any disclaimer, the term of this patent is extended or adjusted under 35 U.S.C. 154(b) by 0 days.

(21) Appl. No.: 09/099,017

(22) Filed: Jun. 17, 1998

(51) Int. Cl.$^7$ ..................................................... A61K 39/00

(52) U.S. Cl. ................................... 424/277.1; 424/279.1; 424/184.1; 424/185.1

(58) Field of Search .......................... 514/55; 424/184.1, 424/185.1, 277.1, 279.1

(56) References Cited

U.S. PATENT DOCUMENTS

| | | | |
|---|---|---|---|
| 4,372,883 | 2/1983 | Matuhashi et al. | 260/112 R |
| 4,446,122 | 5/1984 | Chu et al. | 424/1.1 |
| 4,814,169 | 3/1989 | Mitsuhashi et al. | 424/85.8 |
| 4,877,611 | 10/1989 | Cantrell | 424/88 |
| 4,971,956 | 11/1990 | Suzuki et al. | 514/55 |
| 5,516,639 | 5/1996 | Tindall et al. | 435/7.4 |
| 5,648,478 | 7/1997 | Henderson | 536/241 |
| 5,738,867 | 4/1998 | Spitler | 424/450 |
| 5,925,362 | 7/1999 | Spitler et al. | 424/277.1 |

FOREIGN PATENT DOCUMENTS

| | | |
|---|---|---|
| 0 652 014 A1 | 5/1995 | (EP) . |
| 95/04548 | 2/1995 | (WO) . |
| 96/09805 | 4/1996 | (WO) . |

OTHER PUBLICATIONS

Armbruster, D.A., "Prostate–Specific Antigen: Biocehmistry, Analytical Methods and Clinical Application," Clin. Chem., 39/2:181–195 (1993).
Chen, B. P. et al., "Presentation of Soluble Antigen to Human T Cells by Products of Multiple HLA–Linked Loci: Analysis of Antigen Presentation by a Panel of Cloned, Autologous, HLA–Mutant Epstein–Barr Virus–Transformed Lymphoblastoid Cell Lines," Human Immunology, 18:75–91 (1987).
Cheson, B.D. et al., "Clinical Trials," Oncology, 11(1):81–83 and 90 (Jan., 1997).
Correale, P. et al., "In Vitro Generation of Human Cytotoxic T Lymphocytes Specific for Peptides Derived From Prostate–Specific Antigen," Journal of the National Cancer Institute, 89(4):293–300 (Feb., 1997).
Edelman, R., "Vaccine Adjuvants," Reviews of Infectious Diseases, 2(3):370–383 (May–Jun., 1980).
Fenton, R.G. et al., "Danger Versus Tolerance: Paradigms for Future Studies of Tumor–Specific Cytotoxic T Lymphocytes," Journal of National Cancer Institute, 89(4):272–275 (Feb., 1997).

Freund, J. et al., "Sensitization and Antibody Formation after Injection of Tubercle Bacilli and paraffin Oil," Proc. Soc. Exp. Biol. Med. 37:509–513 (1937).
Gajewski, T.F. et al., "Antiproliferative Effect of IFN–γ in Immune Regulation III. Differential Selection of $T_H1$ and $T_H2$ Murine Helper T Lymphocyte Clones Using Recombinant IL–2 and Recombinant IFN–$γ^{1,}$" J. Immunology, 143:15–22 (Jul., 1989).
Gajewski, T.F. et al., "Murine Th1 and Th2 Lcones Proliferate Optimally in Response to Distinct Antigen–Presenting Cell Populations," J. Immunol. 146(6):1750–1758 (Mar., 1991).
Gaugler, B. et al., "Human Gene MAGE–3 Codes for an Antigen Recognized on a Melanoma by Autologous Cytolytic T Lymphocytes," J. Exp. Med., 179:921–930 (Mar., 1994).
Gauthier, E.R. et al. "Characterization of rhesus monkey prostate specific antigen cDNA," Biochimica Biophysica Acta, 1174:207–210 (1993).
GenBank Accession No. AF007544, Homo sapiens prostate–specific membrane antigen (PSM) gene, complete cds. (1998).
GenBank Accession No. M24543, Human prostate–specific antigen (PA) gene, complete cds. (1995).
GenBank Accession No. AB009903, Homo sapiens gene for PTEN/MMAC1, partial cds. (1998).
GenBank Accession No. L78132, Human prostate carcinoma tumor antigen (pcta–1) mRNA, complete cds. (1997).
GenBank Accession No. M18157, Human glandular kallikrein gene, complete cds. (1996).
GenBank Accession No. L41498, Homo sapiens longation factor 1–alpha 1 (PTI–1) mRNA, complete cds. (1998).
GenBank Accession No. AF043498, Homo sapiens prostate stem cell antigen (PSCA) mRNA, complete cds. (1998).
GenBank Accession No. S57793, Luteinizing hormone receptor [human, ovary, mRNA, 2100 nt]. (1992).
Gery, I. et al., "Stimulation of B–Lymphocytes By Endotoxin: Reaction sof Thymus–Deprived Mice and Karyotypic Analysis of Dividing Cells in Mice Bearing $T_6T_6$ Thymus Grafts," J.Immunology, 108(4):1088–1091 (Apr., 1972).
Grun,J.L. et al., "Different T Helper Cell Subsets Elicited in Mice Utilizing Two Different Adjuvant Vehicles: The Role of Endogenous Interleukin 1 in Proliferative Responses," Cellular Immunology, 121:134–145 (1989).
Gunby, P., "Prostate Cancer's Complexities of Causation, Detection, and Treatment Challenge Researchers," JAMA, 277(20):1580–1582 (May, 1997).
Gupta, R.K. et al., "Adjuvants–a balance between toxicity and adjuvanticity," Vaccine, 11:291–306 (1993).

(List continued on next page.)

Primary Examiner—Sheela Huff
(74) Attorney, Agent, or Firm—Marshall, O'Toole, Gerstein, Murray & Borun

(57) ABSTRACT

The present invention related generally to materials and methods for reduction and/or alleviation of prostatic and prostatic-related (metatastic) carcinoma via the administration of disclosed compositions, immunotherapeutic agents, or antibodies.

4 Claims, 9 Drawing Sheets

OTHER PUBLICATIONS

Hadari, Y.R. et al., "Galectin–8," *Journal Biological Chemistry*, 270(7):3447–3453 (Feb., 1995).

Hodge, J.W. et al., "A Recombinant Vaccinia Virus Expressing Human Prostate–Specific Antigen (PSA): Safety and Immunogenicity in a Non–Human Primate," *Int. J. Cancer*, 63:231–237 (1995).

Hrouda, D. et al., "Gene therapy for prostate cancer," *Gene Therapy*, 3:845–852 (1996).

Jia, X–C et al., "Expression of Human Luteinizing Hormone (LH) Receptor: Interaction with LH and Chorionic Gonadoptropin from Human but not Equine, Rat, and Ovine Species," *Molecular Endocrinology*, 5:759–768 (1991).

Johnson, A.G. et al., "Studies on the O Antigen of *Salmonella Typhosa* V. Enhancement of Antibody Response to Protein Antigens by the Purified Lipopolysaccharide," *J. Exp. Med.* 103:225–246 (1956).

Kong, D. et al., "PTEN1 is frequently mutated in primary endometrial carcinomas," *Nature Genetics*, 17:143–144 (Oct., 1997).

Lundwall, A., "Characterization of the gene for Prostate–specific antigen, a human galndular–kallikrein," *Biochemical Biophysical Research Communications*, 161(3):1151–1159 (Jun. 30, 1988).

Marcinkiewicz, J. et al., "Immunoadjuvant Properties of Chitosan," *Archivum Immunologiae et Therapeae Experimentalis*, 39:127–132 (1991).

Mosmann, T.R. et al., "TH1 and TH2 Cells: Different Patterns of Lymphokine Secretion Lead to Different Functional Properties," *Ann. Rev. Immunol.* 7:145–173 (1989).

Murphy, G.P. et al., "Measurement of Prostate–Specific Membrane Antigen in the Serum With a New Antibody," *Prostate*, 28:266–271 (1996).

Murphy, G. et al., "Comparison of Prostate Specific Membrane Antigen, and Prostate Specific Antigen Levels in Prostatic Cancer Patients," *Anticancer Research*, 15:1473–1480 (1995).

Nishimura, K. et al., "Immunological activity of chitin and its derivatives," *Vaccine*, 2:93–99 (Mar., 1984).

Ohta,, M. et al., Adjuvant action of bacterial lipopolysaccharide in induction of delayed–type hypersensitivity to protein antigens. II. Relationships of intensity of the action to that of other immunological activities, *Immunobiology 163:*460–469 (1982).

Ramanathan, V.D. et al., "Complement activation by aluminum and zirconium compounds," *Immunology*, 37:881–888 (1979).

Reiter, E. et al., "Expression and Functionality of Luteinizing Hormone/Chorionic Gonadotropin Receptor in the Rat Prostate," *Endocrinology*, 136(3):917–922 (1995).

Reiter, R.E. et al., "Prostate stem cell antigen: A cell surface marker overexpressed in prostate cancer," *Proc. Natl. Acad. Sci.*, USA, 95:1735–1740 (Feb., 1998).

Ressing, M.E. et al., "Human CTL Epitopes Encoded by Human Papillomavirus Type 16 E6 and E7 Identified Through In Vivo and In Vitro Immunogenicity Studies of HLA–A*0201–Binding Peptides," *Journal Immunology*, 154:5934–5943 (1995).

Riegman, P.H.J. et al., "Characterization of the Prostate–Specific Antigen Gene: A Novel Human Kallikrein–Like Gene," *Biochemical Biophysical Research Communications*, 159(1):95–102 (Feb., 1989).

Robbins, P.F. et al., "A Mutated β–Catenin Gene Encodes a Melanoma–specific Antigen Recognized by Tumor Infiltrating Lymphocytes," *J. Exp. Med.*, 183:1185–1192 (Mar., 1996).

Sakurada, A. et al., "Infrequent Genetic Alterations of the PTEN/MMAC1 Gene in Japanese Patients with Primary Cancers of the Breast, Lung, Pancreas, Kidney, and Ovary," *Jpn. J.Cancer Res.*, 88:1025–1028 (Nov., 1997).

Salgaller, M.L. et al., "Dendritic Cell–Based Immunotherapy of Prostate Cancer," *Critical Reviews in Immunology*, 18:109–119 (1998).

Schedlich, L.J. et al., "Primary Structure of a Human Glandular Kallikrein Gene," *DNA*, 6(5):429–437 (1987).

Sharief, F.S. et al., "Human Prostatic Acid Phosphatase: cDNA CLoning, Gene Mapping and Protein Sequence Homology with Lysosomal Acid Phosphatase," *Biochemical Biophysical Research Communications*, 160(1):79–86 (Apr., 1989).

Shen, R. et al., "Identification of the human prostatic carcinoma oncogene PTI–1 by rapid expression cloning and differential RNA display," *Proc. Natl. Acad. Sci.*, USA, 92:6778–6782 (Jul., 1995).

Siskind, G.W., "Manipulation of the Immune Response," *Pharmacological Reviews*, 25(2):319–324 (1973).

Talwar, G.P. et al., "Vaccines for Control of Fertility and Hormone Dependent Cancers," *Int. J.Immunopharmac.*, 14(3):511–514 (1992).

Tao, Y.X. et al., "Novel expression of luteinizing hormone/chorionic gonadotropin receptor gene in rat prostates," Molecular and Cellular Endocrinology, 111:R9–R12 (1995).

Tomai, M.A. et al., "T Cell and Interferon–γ Involvement in the Adjuvant Action of a Detoxified Endotoxin," *J. Biological Response Modifiers*, 8:625–643 (1989).

Towbin, H. et al., "Electrophoretic transfer of proteins from polyacrylamide gels to nitrocellulose sheets: Procedure and some applications," *Proc. Natl. Acad. Sci.,*USA 76(9):4350–4354 (Sep., 1979).

van der Bruggen, P.et al., "A Gene Encoding an Antigen Recognized by Cytolytic T Lymphocytes on a Human Melanoma," *Science*, 254:1643–1647 (Dec., 1991).

Warren, H.S. et al., "Current Status of Immunological Adjuvants," *Ann. Rev. Immunol.*, 4:369–388 (1986).

White, R.G. et al., "Studies on Antibody Production III. The Alum Granuloma," *J. Exp. Med.*, 102:73–82 (1955).

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "5' Primer"

(xi) SEQUENCE DESCRIPTION: SEQ ID NO:1:

TAACCCGGGA ATTCATTCCG CCGGAGAGCT GTGTC      35

(2) INFORMATION FOR SEQ ID NO:2:

(i) SEQUENCE CHARACTERISTICS:
      (A) LENGTH: 34 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "3' Primer"

(xi) SEQUENCE DESCRIPTION: SEQ ID NO:2:

TAACCCGGGA ATTCCTTGAG TCTTGGCCTG GTCA      34

(2) INFORMATION FOR SEQ ID NO:3:

(i) SEQUENCE CHARACTERISTICS:
      (A) LENGTH: 19 base pairs
      (B) TYPE: nucleic acid
      (C) STRANDEDNESS: single (D) TOPOLOGY: linear (ii) MOLECULE TYPE: other nucleic acid
        (A) DESCRIPTION: /desc = "Reverse primer"

(xi) SEQUENCE DESCRIPTION: SEQ ID NO:3:

GGAAACAGCT ATGACCATG                                                    19

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "M13-20 primer"

(xi) SEQUENCE DESCRIPTION: SEQ ID NO:4:

GTAAAACGAC GGCCAGT                                                      17

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SpeI adaptor"

(xi) SEQUENCE DESCRIPTION: SEQ ID NO:5:

CCAACCCCAC TAGTGGGGTT GG                                                22

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "SpeI primer"

(ix) FEATURE:
        (A) NAME/KEY: misc_feature
        (B) LOCATION: 1..22
        (D) OTHER INFORMATION: /note= "As presented in the Sequence
            Listing the nucleotide sequence reads in the 5' to 3'
            direction. As presented in the specification the
            sequence reads in the 3' to 5' direction.

(xi) SEQUENCE DESCRIPTION: SEQ ID NO:6:

CCAACCCCAC TAGTGGGGTT GG                                                22

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear -continued

```
  (ii) MOLECULE TYPE: other nucleic acid
       (A) DESCRIPTION: /desc = "His6x tag"

(xi) SEQUENCE DESCRIPTION: SEQ ID NO:7:

CACCACCATC ACCACCAT                                                    18
```

METHODS AND MATERIALS FOR THE TREATMENT OF PROSTATIC CARCINOMA

BACKGROUND OF THE INVENTION

1. Field of the Invention

The invention relates generally to methods for the treatment of neoplastic diseases and, more specifically, to an immunotherapeutic agent comprising a prostate-associated-antigen in conjunction with a chitosan-based adjuvant and its use in the treatment of prostatic carcinoma.

2. Related Technology

Prostatic carcinoma is one of the most common malignancies of men and a leading cause of death in this population. Worldwide it is an important public health concern as over a quarter of a million new cases were diagnosed in 1985 alone. Within the United States, it was predicted that for 1994, 38,000 individuals would succumb to prostate cancer, while in the countries of the European Union it was predicted the disease would account for more than 35,000 deaths. If detected at an early stage, prostate cancer is potentially curable. Its relatively slow growth and androgen dependence distinguish it from most other carcinomas. The disease exhibits an improved prognosis when detected in an early stage, although a majority of cases are diagnosed at later stages, where metastasis of the primary tumor has already occurred. Five year survival rates for patients with prostate cancer range from 88% for those with localized disease to 29% for those with metastatic disease.

Present treatments for prostatic carcinoma include simply monitoring the disease, to radical prostatectomy, radiation therapy, or hormonal therapy. Simple monitoring of the disease is advocated as a reasonable approach for some patients with prostate cancer. Although untreated prostate cancer continues to grow, it may do so quite slowly. Specifically, the growth of the cancer may be slow enough that it causes no problems in a particular individuals lifetime, even if left untreated. While no one can predict exactly how long it will take for a specific cancer to spread or how long a particular individual's lifespan would be, unless an individual is expected to live at least 10 years, simply monitoring with no immediate treatment may be appropriate when the cancer is small and of low grade. If the prostatic cancer is of a higher grade and thus more aggressive then the cancer may be a significant threat to life or health within 10 years and therefore a more aggressive approach to management would be warranted.

Surgery performed for treatment of localized prostate cancer is referred to as a radical prostatectomy. Through an incision in the lower abdomen or below the scrotum, the entire prostate and seminal vesicles are removed. When the carcinoma is confined within the tissues removed during surgery, a radical prostatectomy completely alleviates localized prostate cancer. Such surgery is of little therapeutic value once the cancer has metastasized to the areas surrounding the prostate as well as distant areas of the body. Further, such surgery may leave the individual permanently impotent.

As an alternative to surgery, radiation therapy may be indicated. Specifically, radiation is recommended for men in whom the disease has spread outside of the prostate capsule (and thus making surgery more difficult) but is still localized within the tissues surrounding the prostate capsule. Side effects such as hair loss and lethargy after irradiation have been well documented.

Another form of treatment for prostatic carcinoma involves hormone therapy. Specifically and as prostate cancer has been shown to be under the trophic influence of androgen hormones, androgen deprivation may often produce a regression of the disease and improvement of symptoms. The goal of androgen deprivation is to achieve castration levels of testosterone and dihydrotestosterone. This goal is usually attained by one of four methods: (1) surgical castration (orchiectomy); (2) administration of exogenous estrogens such as diethylstilbestrol (DES); (3) use of analogs of luteinizing hormone-releasing hormone (LHRH) that inhibit the release of pituitary gonadotropins; or (4) the use of anti-androgens, such as flutamide, that block the action of androgens at target tissues. Hormonal therapy is usually used when there is evidence that the cancer has spread beyond the prostate. It is important to note that hormonal therapy is not considered curative. Specifically, the cancer eventually becomes resistant to hormone deprivation and continues to grow. Further, it has been noted in most patients receiving anti-androgen therapy, such therapy will result in the disease becoming hormone independent.

In view of the limitations of the current therapeutic approaches to the treatment of prostatic carcinoma, there remains a need for a more suitable treatment that could be used to alleviate prostate cancer (either localized or metastasized) that is neither invasive nor produces the unwanted side effects of the currently available treatments.

SUMMARY OF THE INVENTION

The present invention is directed to compositions comprising one or more prostate-associated antigens and a chitosan-metal chelate adjuvant. The compositions may be used in methods for producing antibodies against prostate-associated antigens and/or may be used as agents immunotherapeutic agent. In another aspect, the invention is directed to methods for producing compositions comprising one or more prostate-associated antigens and a chitosan-metal chelate adjuvant as well methods for inhibiting the growth or alleviating prostate cancer or metastatic carcinoma of prostatic origin. The invention is also directed to immunotherapeutic agents comprising one or more prostate-associated antigens in combination with a chitosan-metal chelate adjuvant.

As yet another aspect, the present invention is directed to antibody substances (that specifically binds a prostate-associated antigen) produced by the process of administering the one or more specific prostate-associated antigens in combination with the chitosan-metal chelate adjuvant. The invention is further directed to methods for the production of such antibody substances.

The present invention is also directed to compositions comprising one or more prostate-associated antigens and a chitosan/sodium hydroxide/oil/surfactant adjuvant. The compositions may be used in methods for producing antibodies against prostate-associated antigens and/or may be used as immunotherapeutic agents. In another aspect, the invention is directed to methods for producing compositions comprising one or more prostate-associated antigens and a chitosan/sodium hydroxide/oil/surfactant adjuvant as well methods for inhibiting the growth or alleviating prostate cancer or metastatic carcinoma of prostatic in origin. The invention is also directed to immunotherapeutic agents comprising one or more prostate-associated antigens and a chitosan/sodium hydroxide/oil/surfactant adjuvant.

As yet another aspect, the present invention provides antibody substances (that specifically binds a prostate-associated antigen) produced by the process of administering the specific prostate-associated antigen in combination with the chitosan/sodium hydroxide/oil/surfactant based adjuvant. The invention is further directed to methods for the production of such antibody substances.

In another of its aspects, the present invention is further directed to a composition comprising one or more prostate-associated antigens and a phosphate buffer/chitosan-based adjuvant. The composition may be used in methods for producing antibodies against prostate-associated-antigens and/or may be used as immunotherapeutic agents. In another aspect, the invention is directed to methods for producing compositions comprising one or more prostate-associated antigens in combination with a phosphate buffer/chitosan-based adjuvant as well methods for inhibiting the growth or alleviating prostate cancer or metastatic carcinoma of prostatic in origin. The invention is also directed to an immunotherapeutic agent comprising one or more prostate-associated antigens and a phosphate buffer/chitosan-based adjuvant.

As yet another aspect, the present invention is directed to antibody substances (that specifically binds a prostate-associated antigen) produced by the process of administering the one or more prostate-associated antigens in combination with the phosphate buffer/chitosan-based adjuvant. The invention is further directed to methods for the production of such antibody substances.

Other objectives and advantages of the invention may be apparent to those skilled in the art from a review of the following detailed description, including any drawings, as well as the approved claims.

DETAILED DESCRIPTION OF THE INVENTION

Figure 1:
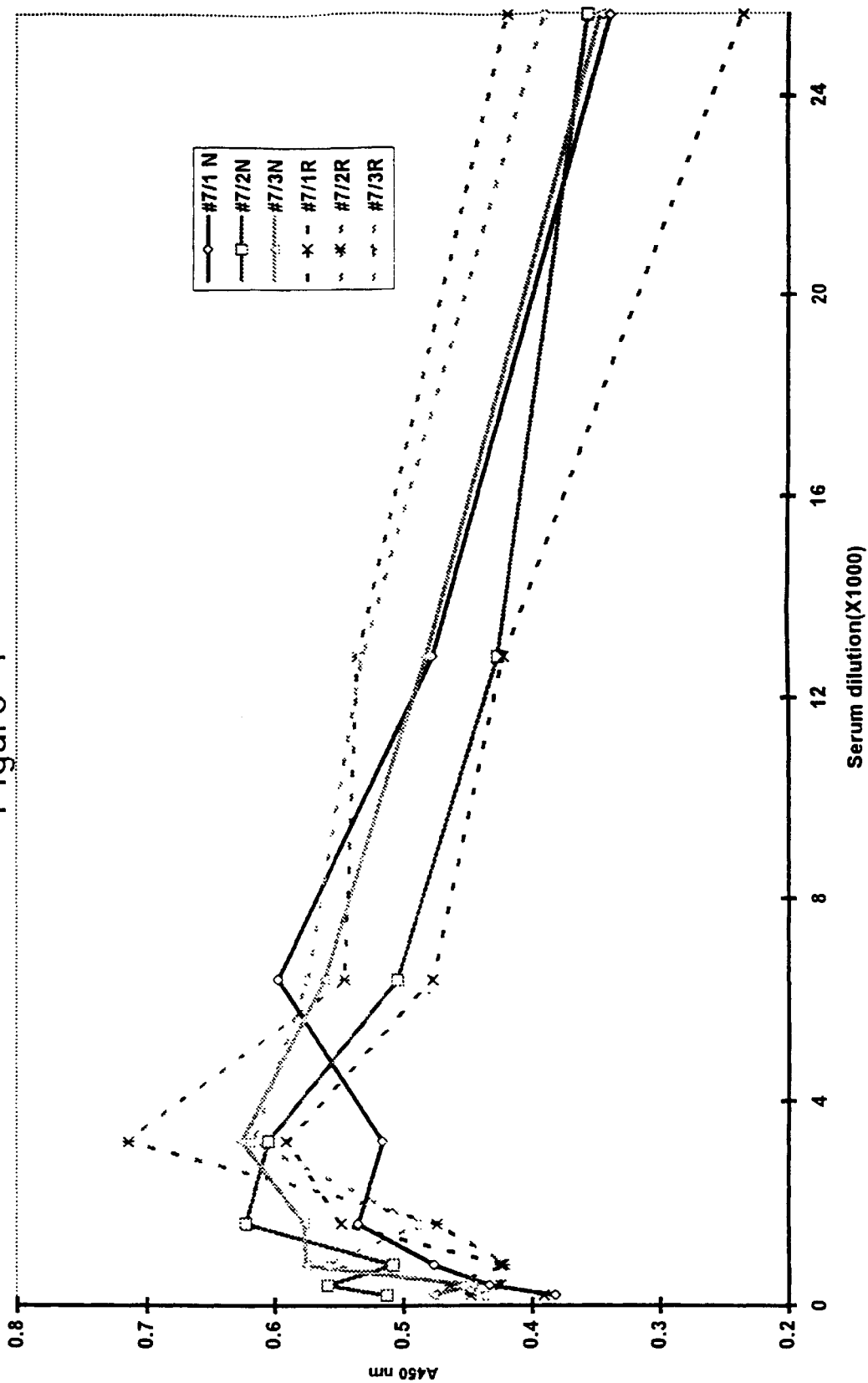
FIG. 1 illustrates the antibody titers obtained from rats immunized with recombinant PSA/chitosan-zinc chelate as well as the titer of the antisera obtained with native PSA.

The prostate is a gland of the male reproductive system. It is a walnut-sized organ, made up largely of muscular and glandular tissues, located between the bladder and the urethra. Its main function is to produce fluid for semen. Specifically, the prostate secretes a thin, milky, alkaline fluid containing citric acid, calcium, acid phosphate, a clotting factor, and a profibrinolysin. During emission, the capsule of the prostate gland contracts simultaneously with the contractions of the vas deferens so that the thin, milky fluid of the prostate gland adds to the bulk of the semen.

Over 95% of the prostatic carcinomas are adenocarcinomas that arise in the prostatic acini. Adenocarcinoma may begin anywhere in the prostate but has a predilection for the periphery. The tumors are frequently multifocal. Variability in cellular size, nuclear and nucleolar shape, glandular differentiation, and the content of acid phosphatase and mucin may occur within a single specimen, but the most poorly differentiated area of tumor (i.e., its area with the highest histologic grade) appears to determine its biologic behavior. The remaining prostatic cancers are divided among squamous cell and transitional cell carcinomas that arise in the prostatic ducts, carcinoma of the prostatic utricle, carcinosarcomas that arise in the mesenchymal elements of the gland, and occasional metastatic tumors (usually carcinoma of the lung, melanoma, or lymphoma).

Although given the enormous antigenic diversity of the many forms of cancer, the identification of all tumor antigens that possess protective potential is a formidable task, a number of human clinical trials are currently underway to assess the efficacy of treating human tumors by immunotherapeutic means.

This type of therapy (cancer immunotherapy) is based upon the recent and expanding identification of specific therapeutic targets: tumor antigens with various degrees of association with their normal counterparts. These targets can be grouped into four general categories: (1) the "cancer/testis" antigens, such as the MAGE gene family, whose expression is tumor specific except for spermatogonia and whose genes have been mapped to the X chromosome [van der Bruggen et al., *Science*, 254:1643 (1991); Gaugler et al., *J. Exp. Med.*, 179:921 (1994)]; (2) virally derived antigens, including herpesvirus [Ressing et al., *J. Immunol.*, 154:5934 (1995)] and Epstein-Barr virus [Chen et al., *Hum. Immunol.*, 18:75 (1987)]; (3) differentiation antigens, including prostate specific antigen [Murphy et al., *Anticancer Res.*, 15:1473 (1995)] and prostate specific membrane antigen [Murphy et al., *Prostate*, 28:266 (1996)]; and (4) antigens existing in a modified or mutated form in tumor as compared to normal cells [Robbins et al., *J. Exp. Med.*, 183:1185 (1996)].

Whereas vaccination aims to prevent tumor formation, the goal of immunotherapy is to augment a patient's immune responses to an established tumor.

Because specific tumor antigens have not yet been identified or isolated from most human cancers, most forms of immune intervention attempt to enhance a patient's overall level of immunity with nonspecific immunopotentiators. However, several recent advances in basic biology have revived interest in active specific immunotherapy. It has become possible to identify, isolate, and characterize tumor antigens that are recognized by T cells in the context of MHC (major histocompatibility complex) class I or class II determinants. Such T cell-defined tumor antigens are likely to be better candidates for use in immunotherapeutic methods than epitopes identified with tumor-specific antibodies, given the greater over-all importance of cells over antibodies in antitumor immunity. Some of the T cell-defined antigens are expressed in different tumors of related tissue and cellular origins; this eliminates the need for autologous tumor tissue for immunotherapeutic development.

Types of cancer immunotherapy include (1) whole cell vaccines, (2) viral oncolysates, (3) partially purified tumor antigen vaccines, and (4) highly purified or synthetic tumor antigen vaccines. Whole tumor cells display not one but all of the potential antigens expressed by the cancer cells, as such they can function as antigen presenting cells. In addition they can be engineered to express tumor antigens or to produce cytotoxic cytokines. Viral oncolysates, used as cancer vaccines, are virus augmented tumor cell lysates. Tumor cells are infected with an appropriate virus utilizing modem cell culture techniques. Partially purified tumor antigen vaccines are prepared from material shed into a culture medium from multiple cell, which express tumor antigens. In excluding much of the cellular material the vaccine is said to be partially purified. While the foregoing approaches to cancer immunotherapy have been evaluated for a number of different cancer types, none have resulted in success in clinical trials.

With respect to the use of highly purified or synthetic tumor antigen vaccines, there is an inherent tolerance to cancer antigens in patients that must be overcome in order to ensure effectiveness. In order to overcome immune tolerance, vaccine design should be directed toward enhancing the host's immune response to purified or synthetic antigens. The present invention addresses this problem by providing a novel antigen-adjuvant composition (i.e., an immunotherapeutic agent) comprising a prostate-associated antigen in conjunction with an adjuvant system, which results in the inhibition of growth and incidence of prostate carcinoma.

The tissue specificity of prostate-related antigens such as PSA, PSMA, HK2, PCTA-1, PTI-1, PSCA, PAP, PTEN/MMAC1, and the LH receptor make them potential target antigens for active specific immunotherapy. Prostate-specific antigen (PSA) is a 240 amino acid glycoprotein produced by nonnal prostate tissue. It is a serine protease and belongs to the glandular kallikrien gene family [Lundwall et al, *Biochem. Biophys Res. Comm.*, 161:1151–1159 (1988)]. PSA's absolute tissue specificity makes it a valuable as a tumor marker for prostate cancer. Previously, prostatic acid phosphatase (PAP) was used to aid in the diagnosis of prostate cancer as well as to monitor the efficacy of therapy for prostate cancer. PAP has now been replaced by PSA for use in the diagnosis of prostate cancer because of PSA's greater sensitivity. PSA is useful for monitoring therapy, particularly surgical prostectomey, because complete removal of the prostate gland should result in undetectable levels of PSA. Measurable PSA after radical prostectomy indicates residual prostate tissue or metastasis and increasing PSA concentrations indicate recurrent disease.

A primary concern involving the development of an immunotherapeutic agent for the treatment of prostate cancer is whether an active immune response can be generated to a self-polypeptide such as PSA. Controlled immunization for the purpose of stimulating antibody production by B cells is dependent upon a myriad of factors inherent to both the antigen itself and the immunized individual. In general, the farther removed in evolutionary terms the antigen, or its source, is from the invaded host, the more effective the immune response elicited by the antigen. Antigens derived from closely related species are less competent in eliciting antibody production due to the fact that the host immune system is unable to clearly distinguish the foreign antigen from endogenous, or self antigens. In addition, the dosage of the antigen, the purity of the antigen, and the frequency with which the antigen is administered are also factors which significantly contribute to the resulting antibody titer and specificity of the resulting antibodies. Still other factors include the form, or complexity, of the antigen, and how the antigen is administered. Finally, both the genetic makeup and overall physiological state of the immunized animal contribute to the extent to which an immune response is mounted. Of these factors, the form or complexity of the antigen is directly affected by immunization with an adjuvant.

Ideally, an adjuvant should potentiate long-lasting expression of functionally active antibodies, elicit cell-mediated immunity (CMI), and enhance production of memory T- and B-lymphocytes with highly specific immunoreactivity against an invading antigen. More important is the ability of an adjuvant to augment the immune response with a minimum of toxic side effects. Therefore, efficacy of an adjuvant is described in terms of how it balances positive (potentiated immunity) and negative (toxicity) effects.

Current understanding suggests that adjuvants act to augment the immune response by a variety of different mechanisms. In one mechanism, the adjuvant directly stimulates one of either CD4$^+$ helper T-cell subpopulations designated $T_H1$ or $T_H2$ [osmann and Coffman, *Ann.Rev.Immunol.* 7:145–173 (1989)]. Helper T cells are required for B-cell antibody responses to most antigens. Alum, an aluminum salt adjuvant approved for clinical use in humans, has been reported to selectively activate $T_H2$ cells in mice [Grun and Maurer, *Cell.Immunol.* 121:134–145 (1989)], while Freund's complete adjuvant (FCA), an emulsion of mineral oil with killed mycobacteria [Freund, et al. *Proc.Soc.Exp.Biol.Med.* 37:509 (1937)], preferentially activates murine $T_H1$ cells [Grun and Maurer, *Cell.Immunol.* 121:134–145 (1989)]. The nature of the cytokine production in activated T-cells may also be influenced in part by the choice of adjuvant.

Another mechanism by which the immune response is augmented involves the direct stimulation of B cells by certain antigens, for example, lipopolysaccharide (LPS) from Gram-negative bacteria. [Gery, et al., *J.Immunol.* 108:1088 (1972)]. LPS has also been shown to stimulate secretion of interferon-γ (INF-γ) [Tomai and Johnson, *J.Biol.Resp.Med.* 8:625–643 (1989)], which both inhibits proliferation of $T_H2$ cells and stimulates differentiation of $T_H1$ cells [Gajewski, et al., *J.Immunol.* 143:15–22 (1989); Gajewski, et al., *J.Immnunol.* 146:1750–1758 (1991)]. The mechanism by which LPS potentiates the immune response is therefore through direct stimulation of B cells, and indirect regulation of both $T_H1$ and $T_H2$ cell populations.

Still other modes of immunopotentiation have been reported for other adjuvants. Oil emulsions (i.e., Freund's complete adjuvant [FCA], Freund's incomplete adjuvant [FIA]) and liposomes act through depot formation as does alum, thus allowing for slow release of antigen. Slow release of antigen permits extended exposure of the antigen to the immune system and also allows for initial immunization with a dosage of antigen that, if delivered at one time, would ordinarily be counterproductive to antibody formation. It has been previously reported that while a large initial dose of antigen results in the production of a higher immediate titer of antibody, the increase in antibody titer and increase in antibody specificity as a function of time is not as great as observed with lower and more frequent doses of antigen [Siskind, G., *Pharm.Rev.* 25:319–324 (1973)]. Therefore, adjuvants which control presentation of an antigen to the immune system modulate antigen dosage in addition to altering the form, or complexity, of the antigen.

To date, only one adjuvant, alum [AlK(SO$_4$)$_2$H$_2$O], has proven sufficiently non-toxic to permit its use in humans. Alum not only acts through T$_H$2 cell activation, depot formation and slow release of antigen following immunization [Edelman, *Rev.Infect.Dis.* 2:370–383 (1980); Warren, et al., *Ann.Rev.Immunol.* 4:369–388 (1986)], but also through granuloma formation by attracting immunocompetent cells [White, et al., *J.Exp.Med.* 102:73–82 (1955)] and activation of complement [Ramanathan, et al., *Immunol.* 37:881–888 (1979)]. However, alum is not without its negative side effects which include erythema, subcutaneous nodules, contact hypersensitivity, and granulomatous inflammation.

Other adjuvants, which are widely employed outside of human application, are also the focus of continuing research to develop acceptable alternatives for use in humans. Included in this group are bacterial products (i.e., LPS, cholera toxin, mycobacterial components and whole killed *Corynebacterium parvum*, *Coiynebacterium granulosum*, and *Bordetella pertussis*, liposomes, immunostimulating complexes (ISCOMs), and naturally occurring and derivatized polysaccharides from other than bacterial sources.

The immunopotentiating capacity of polysaccharides has been a focus of investigation over the past few years as these compounds are widespread in nature, e.g., as structural components in the cell walls of bacteria, and exoskeletons of insects and crustacea. Lipopolysaccharide (LPS) isolated from certain Gram-negative bacteria is one such polysaccharide even though the adjuvant properties of LPS are derived mainly from the lipid A region of the molecule, and not from the o-specific polysaccharide or core oligosaccharide regions of the molecule. LPS, which augments both humoral [Johnson, et al., *J.Exp.Med.* 103:225–246 (1956)] and cell-mediated immunity [Ohta, et al., *Immunobiology* 53:827 (1984)], possesses numerous biological activities, but is impractical for use in humans due to its inherent toxicity [See Gupta, et al., *Vaccine* 11:291–306 (1993)]. Attention has therefore shifted to other polysaccharides including, among others, chitosan.

Chitosan [β-(1-4)-2-amino-2-deoxy-D-glucan] is a derivative of chitin and has been widely used in biomedical applications, due in part to is biodegradability by lysozyme and low toxicity in humans. These same properties have resulted in increased interest in chitosan as an immunopotentiating agent. For example, Matuhashi, et al., in U.S. Pat. No. 4,372,883, disclosed conjugation of soluble polysaccharides, including chitosan, to normally toxic antigens, conjugation thereby detoxifying the antigen and permitting its use as an immunogen. Matuhashi et al., however, did not address the use of insoluble polysaccharide forms of chitosan, nor did Matuhashi compare the resulting serum antibody titer with that obtained from immunization with other known adjuvants.

Likewise, Suzuki, et al., in U.S. Pat. No. 4,971,956, disclosed the use of water soluble chitosan-oligomers as therapeutics for treatment of bacterial and fungal infections, as well as for the treatment of tumors. Suzuki, et al, discussed the difficulty in modifying chitosan to produce an appropriate water soluble form, disclosing that water-insoluble forms are impractical for therapeutic application. In addition, Suzuki et al., does not disclose conjugation of an antigen to chitosan to effect enhanced immune response.

Mitsuhashi, et al., in U.S. Pat. No. 4,814,169, disclosed the use of human protein conjugated to soluble polysaccharides to generate antibodies against human protein in non-human animals. Although Mitsuhashi et al. included chitosan in an exemplary list of polysaccharides, the patent merely predicted that chitosan may be useful for antibody production, and did not provide details regarding the nature of the expected immune response. Further, the '169 patent set forth non-ionic polysaccharides as the preferred saccharides, while chitosan is highly cationic.

Nishimura et al. [*Vaccine* 2:93–99 (1984)] reported the immunological properties of derivatives of chitin in terms of activation of peritoneal macrophages in vivo, suppression of tumor growth in mice, and protection against bacterial infection. Results obtained from their single-injection system showed that both chitin and chitosan were ineffective stimulators of host resistance against challenge with tumor cells or bacteria.

Marcinkiewicz, et al., [*Arch.Immunol.Ther.Exp.* 39:127–132 (1991)] examined the immunoadjuvant activity of water-insoluble chitosan and reported significant enhancement of T-dependent humoral response, but only moderate augmentation of T-independent humoral response. The enhanced humoral response was detected with chitosan at doses of 100 mg/kg administered either intravenously or intraperitoneally. Subcutaneous and oral administration were specifically reported as being ineffective. In addition, Marcinkiewicz, et al., does not suggest conjugation of an antigen to insoluble chitosan, stating that chitosan "resulted in the same response irrespective of the site of administration—either together or separately from antigen."

In view of the foregoing discussion and by way of illustration of the invention, the examples describe an immunotherapeutic agent for the treatment of prostatic carcinoma comprising a prostate-associated antigen and a chitosan-based adjuvant system, and in a preferred embodiment, PSA and a chitosan-zinc chelate-based adjuvant, PSA and a chitosan/sodium hydroxide/squalene/poloxamer 401, or PSA and a phosphate buffer/chitosan-based adjuvant. The Examples set out below demonstrate that this immunotherapeutic agent was successful in reducing and alleviating prostate and prostatic related tumors in subject animals. The illustrative Examples also describe methods for reducing and/or alleviating prostatic carcinoma and prostatic-related carcinoma (metatastic in origin) via the administration of any of the foregoing immunotherapeutic agents The invention is illustrated by the following examples, which are not intended to limit the scope of the invention as recited in the claims.

Example 1 provides methods for the cloning and expression of human PSA.

Example 2 provides methods for the purification of the recombinant form of human PSA.

Example 3 describes the preparation of a chitosan-chelated metal based immunotherapeutic agent involving the use of prostate-related antigens (e.g., PSA, PSMA).

Example 4 describes the preparation of a chitosan-iron chelated based immunotherapeutic agent involving the use of prostate-related antigens (e.g., PSA, PSMA).

Example 5 describes the preparation of an immunotherapeutic agent wherein the prostate-related antigen (e.g., PSA, PSMA) is incorporated and lyophilized in phosphate buffer and reconstituted in a chitosan solution.

Example 6 describes the preparation of an immunotherapeutic agent wherein the prostate-associated antigen (e.g., PSA, PSMA) is incorporated into a chitosan-oil emulsion.

Example 7 describes the characterization of the immune response in rats to administration of either native human PSA/chitosan-zinc chelate or recombinant PSA/chitosan-zinc chelate.

Example 8 demonstrates the specificity of the antibodies to PSA found in the sera of the rats of Example 7 via Western blot analysis.

Example 9 describes the ability of antibodies to PSA found in the sera of the rats of Example 7 to bind to human prostatic carcinoma cells.

Example 10 describes the effect of rat anti-PSA antisera on the proliferation of human prostate cells (in vitro).

Example 11 describes the characterization of the immune response in rats to administration of either native human PSA or recombinant PSA bound to a chitosan-zinc chelate.

Example 12 describes the effect of monkey anti-PSA antisera on the in vitro proliferation of human prostatic carcinoma cells.

Example 13 describes the effect of partially purified monkey anti-recombinant PSA or anti-native PSA antibodies on the in vivo growth of human prostatic carcinoma cells (passive immunization).

Example 14 describes the effect of early administration of purified monkey anti-recombinant PSA or anti-native PSA antibodies on Du145 tumor incidence in athymic mice.

Example 15 describes administration of an immunotherapeutic agent of the present invention to humans to inhibit growth or alleviate prostate cancer or metastatic carcinoma of prostatic origin.

EXAMPLE 1

Cloning and Expression of Human Prostate Specific Antigen (PSA)

Polymerase Chain Reaction

The human PSA gene (with signal sequence) was cloned from human prostate cDNA (Quickclone cDNA lot#6060116; Clontech, Palo Alto, Calif.) using the polymerase chain reaction [PCR; Mullis et al., *The Polymerase Chain Reaction*, Birkhäuser, Boston (1994)]. The sequence of the primers used (see below) was determined based on a published sequence for human PSA [Riegman et al., Biochem. Biophys. Res. Comm. 159(1):95–102 (1989); GenBank Accession No. M24543] and subsequently modified as described below.

Both polymerase chain reaction primers were synthesized using an Applied Biosystems Model 391 DNA Synthesizer (Applied Biosystems, Foster City, Calif.) and standard protocols for solid phase DNA synthesis. Specifically, The 5' primer contained 21 bases of 5' untranslated region with the addition of SmaI and EcoRI restriction enzyme sites for subcloning into sequencing and/or expression vectors [all restrictions enzymes were obtained from New England Biolabs, Beverly, Mass.]. The 3' primer consisted of a 34 base pair oligonucleotide containing 20 bases of 3' untranslated region 50 bases downstream of the stop codon. Similarly, SmaI and EcoRI restriction enzyme sites were also included in this primer for subcloning purposes. The sequence of both PCR primers are as follows:

5' Primer

5'    TAACCCGGGAATTCATTCCGCCG-GAGAGCTGTGTC 3' (SEQ ID NO. 1)

3' Primer

5' TAACCCGGGAATTCCTTGAGTCTTGGCCTGGTCA 3' (SEQ ID NO. 2).

Conditions for the polymerase chain reaction were as follows. 2 μl of prostate cDNA (2 ng; Clontech, Palo Alto, Calif.) were added to a 0.5 ml microfuge tube containing 10 μl 5×PCR reaction buffer (15 mM $MgCl_2$, 500 mM KCl, 100 mM Tris-HCL, pH 8.3, 0.01% gelatin, 2 mM each dNTP), 1 μl 5' primer (20 pmol), 1 μl 3' primer (20 pmol), 1 μl Taq DNA polymerase (Perkin-Elmer Cetus, Branchburg, N.J.), and 35 μl nuclease-free dionized water. The polymerase chain reaction was performed using a Perkin-Elmer Cetus Thermal Cycler (Model PCR Mate, Perkin-Elmer Cetus, Branchburg, N.J.) with 40 cycles of amplification. Each cycle consisted of a 45 second denaturation step at 94° C., a 1 minute annealing step at 58° C., and a 1 minute extension step at 72° C. After completion of 40 cycles, a final 5 minute extension at 72° C. was performed. The polymerase chain reaction resulted in the amplification of an approximately 900 base pair product, as determined by gel electrophoresis, which is the correct size for DNA encoding human PSA.

Subcloning of Human PSA into pBluescript SK Sequencing Vector

The 900 base pair polymerase chain reaction product described above was purified from a 1% TAE agarose gel (0.04 M Tris-acetate, 0.001 M EDTA, pH=8.0, 1% agarose) using a GeneClean® kit (BIO101, Vista, Calif.) into 25 μl TE (10 mM Tris, 1 mM EDTA, pH=8.0). The DNA was subsequently digested with the SmaI restriction enzyme, extracted with phenol:chloroform (1:1 vol/vol.), and precipitated with ½ volume of 7.5 M ammonium acetate and 2 volumes of 95% ethanol at −70° C., for 30 minutes. The DNA was pelleted by centrifugation at 14,000 rpm in an Eppendorf model 5415C microcentrifuge (Eppendorf, Hamburg, Germany), washed with 70% ethanol, and air dried. The DNA was resuspended in 10 μl TE (pH=8.0). SmaI digested human PSA cDNA (PCR product) was next ligated into the SmaI site of pBluescript SK vector (Stratagene, LaJolla, Calif.). After ligation, the pBluescript vector containing the human PSA cDNA insert was transformed into *E. coli* strain TOPP2 (Stratagene, LaJolla, Calif.) by standard transformation protocols. An *E. coli* clone was isolated containing the above described pBluescript/human PSA vector, which was subsequently used to generate further DNA for subsequent experimentation. The human PSA insert was verified by restriction enzyme mapping using known internal restriction enzyme sites of the published human PSA sequence and restriction enzyme sites of the vector that flank the human PSA cDNA insert (either on 5' or 3' end), as well as performing agarose gel electrophoresis to verify observed band size with expected band size. The identity of the human PSA cDNA insert was also verified by partial sequencing using the M13-20 and Reverse primer set Stratagene, LaJolla, Calif.). The sequences of the sequencing primers is as follows:

Reverse Primer

5' GGAAACAGCTATGACCATG'3 (SEQ ID NO. 3)

M13-20 Primer

5' GTAAAACGACGGCCAGT3' (SEQ ID NO. 4)

The sequence obtained from the human PSA insert (approximately 200 base pairs at each end of the insert) was 100% identical to the known human PSA nucleotide sequence.

Insertion of Human PSA Sequence into A Mammalian Expression Vector

For insertion of human PSA encoding cDNA into the mammalian expression vector, the following methodology was used. A SpeI adaptor was ligated into the unique MscI restriction enzyme site within the pBluescript/human PSA construct, 8 base pairs upstream of the stop codon. The SpeI adaptor was made palindromic to regenerate the 8 base pairs between the MscI site and stop codon (now consisting of a SpeI site). The phosphorylated oligonucleotides used to make the SpeI adaptor were purchased from Genosys (Woodlands, Tex.). The sequence of the SpeI adaptor is as follows:

SpeI Adaptor

Figure 9:
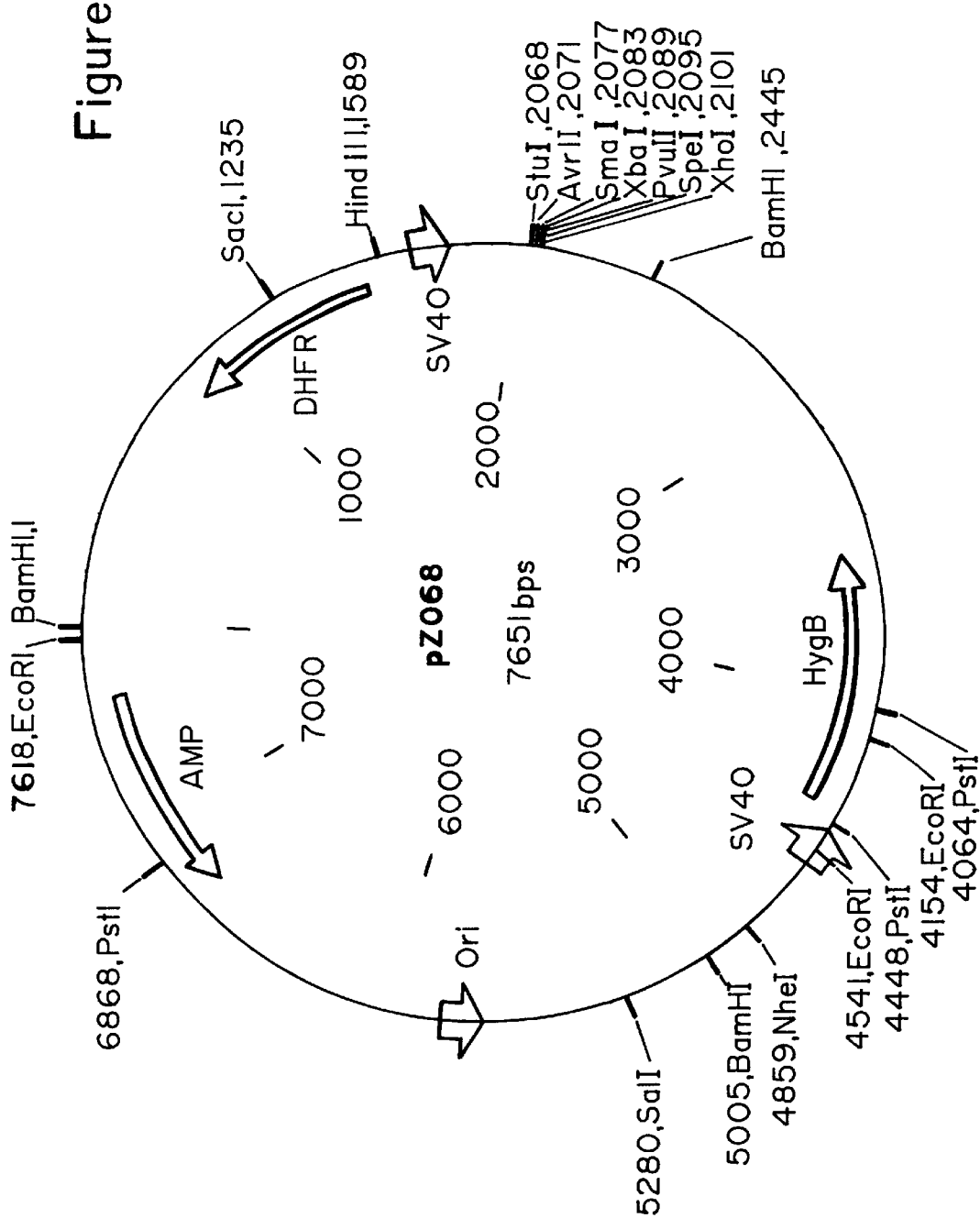
FIG. 9 illustrates the vector map for expression vector pZ068, which was used in Example 1 for the expression of prostate-specific antigen.

5' CCAACCCCACTAGTGGGGTTGG 3' (SEQ ID NO. 5)
3' GGTTGGGGTGATCACCCCAACC 5' (SEQ ID NO. 6).
The complete human PSA sequence was then removed from the pBluescript sequencing vector by digesting with SmaI and SpeI, and subsequently ligating the insert into the PvuII/SpeI restriction enzyme sites of the expression vector pZ068 [which has the DHFR gene cassette, see FIG. 9 for vector map of expression vector pZ068] Lastly, a poly-histidine tag ($His_{6x}$ tag) followed by a stop codon [sequence of $His_{6x}$: 5'CACCACCATCACCACCAT 3' (SEQ ID NO. 7)] were inserted downstream of the generated SpeI site. The resulting PSA insert consisted of the sequence: human PSA-$His_6$ tag-stop codon. This modification resulted in a C-terminal $His_{6x}$ tag fusion on the expressed protein, which allows for the purification of the recombinant PSA using Immobilized Metal Affinity Chromatography (IMAC) as described below.

Transfection of CHO dhfr- Cells with PSA Expression Plasmid

The PSA expression vector (5–10 μg; see directly above) was transfected into dihydrofolate reductase deficient (dhfr⁻) Chinese Hamster Ovary Cells (ATCC, Manassas, Va.) using the following methodology. The pz068 human PSA expression vector was linearized with the SalI restriction enzyme followed by phenol:choloroform (1:1) extraction and precipitation with ½ volume 7.5 M ammonium acetate and 2 volumes of 95% ethanol at −70° C. for 30 minutes. DNA was pelleted by centrifugation at 14,000 rpm in microcentrifuge for 10 minutes, washed with 70% ethanol, and air dried. DNA was resuspended in 10 μl TE (pH=8.0). A transfection mix was prepared by mixing Solution A (10 μl DNA+90 μl Opti MEM (Gibco BRL, Gaithersburg, Md.) with Solution B (10 μl Lipofectamine (Gibco BRL)+90 μl Opti MEM) and incubating the resulting mixture at room temperature for 20 minutes. After incubation, the transfection mix was added to a 35 mm tissue culture dish (Costar, Cambridge, Mass.) containing 2 ml Opti MEM and CHO dhfr⁻ cells at 60–70% confluency. The transfection was allowed to proceed overnight (12–16 hr) at 37° C. and 5% $CO_2$. Immediately following the overnight incubation, the transfection mix was removed and replaced with 2 ml complete Earles MEM (Gibco BRL) containing 5% dialyzed fetal bovine serum (dFBS) and 2 mM L-glutamine (Gibco BRL). Incubation was continued at 37° C. and 5% $CO_2$ for 72 hours. After 72 hours, the cells were removed from the dish by trypsinization and transferred to a T75 tissue culture flask (Costar) containing complete Earles MEM with 5% dFBS (for selection of transfected cells) and 2 mM L-glutamine. The function of the dialyzed serum (which lacks purines) is to select for the cells that contain the plasmid DNA (the expression vector) due to the presence of a DHFR gene cassette present on the vector which compliments the dhfr genotype of the cells (purine biosynthesis deficiency). The dhfr⁻ gene cassette is under control of the constitutive SV40 promoter and codes for dihydrofolate reductase enzyme, which allows for the recovery of purine biosynthesis in CHO dhfr⁻ cells. In the presence of medium that lacks purines (i.e., dialyzed seruin-containing medium) only cells transfected with plasmid DNA (expression vector with dhfr⁻ cassette) will survive.

After selection (1–2 weeks), secretion of PSA was verified by Western blot analysis. Specifically, medium containing PSA was run on a 4–20% polyacrylamide gradient gel (Bio-Rad, Hercules, Calif.) and transferred to nitrocellulose. The resulting blot was blocked in phosphate buffered saline (PBS) containing 0.05% Tween 20 (PBST) and 5% non-fat dry milk, followed by a 1 hour incubation (at room temperature) with primary antibody against human PSA (DAKO Corp., Carpinteria, Calif.). The blot was washed for 5 minutes (3 times) in PBST and subsequently incubated with mouse anti-rabbit secondary antibody at 1:5000 dilution (Zymed, San Francisco, Calif.) for 30 minutes. After three 5 minute washes in PBST, the blot was incubated in PBST containing streptavidin-HRP conjugate at 1:5000 dilution for 20 minutes. The blot was washed three times in PBS for 5 minutes and color was developed using the chromogenic substrate 3-amino-9-ethyl carbazol and hydrogen peroxide.

The heterogeneous population of cells were then cloned by limiting dilution to identify and isolate individual clones that expressed and secreted high levels of recombinant human PSA protein. Once identified and isolated, the clones were scaled up for protein production as described below, as well as frozen for future use.

EXAMPLE 2

Purification of Recombinant PSA

Individual clones of CHO cells secreting recombinant human PSA were grown to confluency in 150 ml Minimal Essential Media (MEM) (Gibco-BRL, Grand Island, N.Y.) supplemented with 5% dialyzed fetal bovine serum (FBS) Hyclone, Logan, Utah) and 2 mM L-glutainine in Triple Flasks (Nunc, Naperville, Ill.). Once confluent, cells were washed with PBS, and media was replaced with PFX-CHO medium (Hyclone). After 72 hours, the medium was removed and centrifuged for 5 min. at 1500×g to remove particulate material, and dialyzed at 4° C. against 5 volumes of 50 mM $NaH_2PO4$, 20 mM Tris, 0.1 M NaCl, pH 8.0, with 3 buffer changes.

After dialysis, media containing secreted PSA was passed through an IMAC column, prepared as follows. First, 5 ml of chelating Sepharose fast flow (Pharmacia, Piscataway, N.J.) was washed 5 times at room temperature with 50 ml of sterile deionized H2O(centrifuging at 1500×g for 5 minutes between each wash). Next, the resin was resuspended in 50 ml 100 mM $CoCl_2$ and mixed for 10 min. at room temperature. The resin was again centrifuged for 5 min at 1500×g and washed 5 times with 50 ml sterile deionized $H_2O$ (centrifuging for 5 min at 1500×g between each wash). After the last wash, the resin was resuspended in 50 ml IMAC binding buffer (50 mM $NaH_2PO_4$ 20 mM Tris, 100 mM NaCl, pH=8.0) and loaded into a 15 ml Econo column (BioRad, Hercules, Calif.). The resin was allowed to settle into the column and an additional 50 ml of binding buffer was passed through the column. After equilibration of the column, the dialyzed media containing human PSA was passed through the column. The column was washed with 20 bed volumes (100 ml) of binding buffer, followed by elution of PSA in 2 bed volumes (10 ml) of PBS containing 200 mM imidazole. Imidazole was removed from the eluate by dialysis in PBS (pH 8.0) and the protein was concentrated to 0.5–2.0 mg/ml using a Centiprep concentrator (Amicon, Beverly, Mass.). The purified concentrated PSA was stored at −70° C. for use in the examples set forth below. In a typical small scale run 5–7 mg of purified recombinant protein could be obtained from 1 liter of medium. Media used for protein production was purchased from Hyclone (PFX-CHO).

EXAMPLE 3

Preparation of Chitosan-Chelated Metal Based Immunotherapeutic Agent

The chitosan-chelated metal based adjuvant was prepared according to the following method. While the zinc is exemplified as the chelated-metal, those of skill in the art will recognize that other metals, such as zinc or copper may be used in the practice of the present invention. Further, while recombinant PSA is exemplified below as the prostate-related antigen, those of skill in the art will recognize that other prostate-related antigens, such as prostate-specific membrane antigen [PSMA; GenBank Accession No. AF007544], human glandular kallikrein-2 [HK2; Schedlich et al., *DNA*, 6:429–437(1987); GenBank Accession No. M18157; see also, U.S. Pat. No. 5,516,639], prostate carcinoma tumor antigen-1 [PCTA-1; Hadari et al., *J. Biol. Chem.*, 270:3447–3453 (1995); GenBank Accession No. L78132], prostate carcinoma tumor inducer-1 [PTI-1; Shen et al., *Proc. Natl. Acad. Sci., USA*, 92:6778–6782 (1995); GenBank Accession No. L41498], prostate stem cell antigen [PSCA; Reiter et al., *Proc. Natl. Acad. Sci., USA*, 95:1735–1740 (1998); GenBank Accession No. AF043498], PTEN/MMAC1 [Kong, et al., *Nature Genet.*, 17:143–144 (1997); Sakurada et al., *Jpn. J. Cancer Res.*, 88:1025–1028 (1997); GenBank Accession No. AB009903 or 2723418], prostate acid phosphatase [PAP; Sharief et al., *Biochem. Biophys. Res. Comm.*, 160:79–86 (1989); GenBank Accession No. M24902], and the LH (luteinizing hormone) receptor [Jia et al., *Mol. Endocrinol.*, 5:759–768 (1991); GenBank Accession No. S57793] may be used in the practice of the present invention To prepare chitosan/metal complex adjuvants containing either zinc, copper or nickel, a 2% chitosan solution was initially prepared by dissolving 2 g chitosan (SeaSanMer N-2000, CTC Organics, Atlanta, Ga.) in 100 ml 2% acetic acid, and the resulting solution was sterilized by autoclaving. As an alternative, the chitosan solution can also be prepared by dissolving 2 g in 100 ml 0.5 M sodium acetate pH 4.5. Solutions of either zinc acetate, nickel sulfate, or copper sulfate solution (although other salts of the metals may be used) were prepared in deionized water at a molarity between 0.001 to 0.2 M and filter sterilized. The 2% chitosan solution was diluted 1:1 using deionized water and 4 ml of the resulting 1% chitosan solution was added to 10 ml of the desired metal salt solution (i.e., either the zinc, nickel, or copper solutions). The resulting suspension was mixed on an end to end shaker for 2 to 4 hours at room temperature. The mixture was then sonicated using a Branson Sonifier 250 for 3 to 5 minutes and the pH of the mixture adjusted to 12.0–12.5 with 10 N NaOH during sonication. When the zinc salt was employed, a white complex precipitate was fonned. When the nickel salt was used, the complex was light green. The copper salt resulted in a blue precipitate. After sonication, the mixture was centrifuged at 2000 rpm (1000×g) for 10 minutes and supernatant discarded. The pellet was washed twice with PBS, pH 7.2, centrifuged after each wash, the wet weight of the pellet determined, and the metal/chitosan complex pellet resuspended in 8 M urea, pH 7.8 to 8.0. The metal/chitosan complexes were either immediately coupled to an antigen, or stored in either 8 M urea or PBS at room temperature. The stored metal/chitosan complexes have shown to be stable for up to six months when stored by this method.

The PSA (may or may not contain a poly-HIS tag), as produced in Example 1, was associated with the metal/chitosan complex by the following method. The chitosan-zinc chelate was equilibrated with phosphate buffered saline (PBS, pH 8.0). Purified recombinant human PSA expressed in CHO cells (see Example 1) was added to the chitosan-zinc chelate suspension and incubated at room temperature for 4 hours. Following incubation, the slurry was centrifuged at 1000 rpm the supernatant was collected and the amount of unbound protein was calculated using the Bradford protein assay (Pierce, Rockford Ill.). During a typical preparation 1.67–0.97 µg of recombinant PSA was found to be bound per mg wet weight of the chitosan-metal chelate. The pellet of immunotherapeutic agent (PSA-poly-HIS and chitosan-zinc chelate) was then resuspended in PBS at a concentration of about 500 µg PSA per ml. The resulting composition was then used in the immunization studies set forth below. The final concentration of the metal in the composition was about 0.7 mM to about 143 mM.

EXAMPLE 4

Preparation of Chitosan-iron Chelate Based Immunotherapeutic Agent

For preparation of a chitosan-iron chelate, 4 g of ferric ammonium citrate is dissolved in 10 ml distilled water with 100 µl 11.6 N HCl. Four ml of the 1% chitosan solution prepared as described above (see Example 3) is sonicated and 200 µl of the ferric ammonium citrate solution is added during sonication. The resulting solution is centrifuged and the pellet containing chitosan-iron chelate is washed once in deionized water and recentrifuged. Recombinant prostate-associated antigen (which may or may not be modified to include six histidine residues) is coupled with the chitosan-iron chelate as above (see Example 3). As with the chitosan-zine chelate composition, the resulting chitosan-ilron chelate composition agent may then be used to immunize individuals for the reduction or alleviation of prostatic carcinoma.

EXAMPLE 5

Preparation of immunotherapeutic Agent Incorporated and Lyophilized in Phosphate Buffer A 0.5 M phosphate buffer is prepared by diluting 15.6 ml of phosphoric acid (16 M; Mallinkrodt Chemical, Paris, Ky.) in 400 ml of deionized (18 mOhm: DI) water. The pH of the solution is adjusted to 7.3 with 10 N sodium hydroxide (Sigma Chemical Co., St. Louis, Mo.). The total volume of the solution is adjusted to 500 ml by the addition of deionized water.

A dilute chitosan solution is made by first preparing a 1% chitosan in 2% acetic acid solution: 1 gm of chitosan (practical grade; Sigma Chemical Co., St. Louis, Mo.) in 100 ml of 2% glacial acetic acid (Mallinkrodt Chemical, Paris, Ky.). The resulting 1% chitosan in 2% acetic acid solution is then diluted further by adding 7.4 ml of the solution to 2.6 ml of deionized water to obtain a working chitosan solution.

A desired amount of prostate-related antigen, such as PSA, PAP, PSMA, HK2, PCTA-1, PTI-1, PSCA, PTEN/MMAC1, or LH receptor (the antigen may or may not contain a poly-HIS tag) is added to a 10 ml vial containing 5 ml of the 0.5 M phosphate buffer. After adding 0.5 gm of d-sorbitol (Sigma Chemical Co., St. Louis, Mo.), the solution is rapidly frozen in liquid nitrogen and lyophilized.

Lyophilized sample is reconstituted with 5 ml of the working chitosan solution, mixed by vortex to fonn a cloudy solution containing white particles, and used for immunization as described below. The pH of the final solution is between 6 and 7.

EXAMPLE 6

Preparation of an Immunotherapeutic Agent Incorparated into a Chitosan-oil Emulsion While the following is exemplified by the use of squalene, those of ordinary skill in the art will appreciate that any oil that is readily metabolized by the recipient animal may be used (e.g., corn, canola, peanut). Further, while the following is exemplified by the use of Pluronic® L121 (poloxamer 401), those of ordinary skill in the art will again appreciate that other surfactants such as sorbitan trioleate, polyoxyethylene sorbitan monooleate, polyoxyethylene sorbitan monolaurate, and polyoxyethylene-20-trioleate may be used, as well as others.

A 2% chitosan solution in 0.5 M sodium acetate is prepared by dissolving 4.1 g of sodium acetate (Sigma Chemical Co., St. Louis, Mo.) in 50 ml of deionized (18 mOhm: DI) water with mixing. The pH of the solution is adjusted to 4.5 with approximately 7 ml of glacial acetic acid (Mallinkrodt Chemical, Paris, Ky.) and an additional 1.5 ml of glacial acetic acid is added to compensate for the effect of the addition of chitosan on the pH of the solution. The total volume of the solution is adjusted to 100 ml by the addition of deionized water. 2 grams of chitosan (Sigma Chemical Co., St. Louis, Mo.) is slowly added to the sodium acetate solution with stirring and the mixture is stirred for 2–3 hours until the chitosan dissolves. The chitosan solution is then sterilized by autoclaving during a 25 minute cycle. The solution is cooled to room temperature in a biosafety cabinet. The chitosan solution is then clarified by centrifugation in an IEC clinical centrifuge (International Equipment Co., Needham Hts., Mass.) at setting 7 for 5 minutes. The supernatant is decanted from the pellet. 87 to 90% (by weight) of the chitosan added is retained in the supernatant.

A 50% sodium hydroxide solution is prepared by dissolving 50 gm of sodium hydroxide (Sigma Chemical Co., St. Louis, Mo.) in 100 ml of deionized water, with mixing. A squalene/surfactant solution is prepared by combining 1500 $\mu$L of squalene (2,6,10,15,19,23-Hexamethyl-2,6,10,14,18,22-tetracosahexane; Sigma Chemical Co., St. Louis, Mo.) with 600 $\mu$L of the surfactant Pluronic® L121 (BASF Corp., Parsippany, N.J.) and is vortexed until homogeneous.

A chitosan/squalene/surfactant/antigen emulsion is prepared by adding a desired amount of a prostate-related antigen, such as PSA, PAP, PSMA, HK2, PCTA-1, PT-1, PSCA, PTEN/MMAC1, or LH receptor (with or without a poly-HIS tag) to approximately 370 $\mu$L of 2% chitosan in 0.5 M sodium acetate and vortexing. The actual amount of antigen used may range from 1 $\mu$g to several milligrams. 10 $\mu$L of the 50% sodium hydroxide are then added to the antigen/chitosan and the sample is vortexed. 10 $\mu$L aliquots of the 50% sodium hydroxide are added until a stable cloudy precipitate forms. Approximately 140 $\mu$L of the previously prepared squalene/surfactant solution are added to the above solution of antigen/chitosan. The resulting solution is vortexed until a cloudy emulsion formed. The final concentration of chitosan ranges from about 0.1% to about 10%, while the final concentration of the oil ranges from about 1% to about 20%. Further, the final concentration of surfactant ranges from about 1% to about 20%. Immediately prior to administration for immunization purposes, the resulting solution of chitosan/squalene/surfactant/antigen is mixed by vortexing or syringe aspiration.

EXAMPLE 7

Immunization and Characterization of the Immune Response in Rats

Sprague-Dawley male rats (Harlan, Houston, Tex.), weighing approximately 250 g, were administered, via intramuscular injection, 25 $\mu$g of the recombinant human PSA/chitosan-zinc chelate (see Examples 1–3 above; 1.67 $\mu$g of recombinant PSA per mg wet weight of chitosan-zinc chelate) per animal. A booster injection of recombinant PSA/chitosan-zinc chelate (25 $\mu$g/animal) was administered 5 weeks subsequent to the initial injection. Animals were bled by retro-orbital puncture and their serum was collected following centrifugation. The resulting antiserum was used in the experiments described below.

Enzyme Linked Immunosorbent Assay (ELISA) plates (Microtest III Flexible Assay Plates, Falcon, Oxnard, Calif.) were coated with either recombinant PSA (produced as described above) or native PSA (PSA purified from human semen, Chemicon Inc., Temecula, Calif.), 50 ng/50 $\mu$l/well in a sodium carbonate buffer, pH=9.6. The nonspecific sites were blocked with 100 $\mu$/well of 2% non-fat dry milk in a sodium carbonate buffer, pH 9.6. The plates were washed 4 times with Phosphate buffered saline containing 0.05% Tween 20, Sigma Chemical Co., St. Louis, Mo.; PBST). The antisera, 50 $\mu$l/well, was added to the wells in a serially-doubling dilution and incubated at 37° C. for at least 3 hr. The plates were washed 4 times with PBST and rabbit-anti-rat biotin conjugate (1:1000 dilution; Zymed, San Francisco, Calif.) was added and further incubated for 3 hours at 37° C. The plates were washed 4 times with PBST and strepavidin-horse radish peroxidase conjugate (1:1000 dilution; Zymed, San Francisco, Calif.) was added and incubated for 1 hour at 37° C. The plates were then washed and substrate solution, ortho-phenylenediamine hydrochloride (8 mg/10 ml in citrate phosphate buffer, pH 5.5 plus 100 $\mu$l of $H_2O_2$) was added. The plates were then read in an ELISA reader (at an optical density of 450 nm). The highest dilution at which no further decrease in absorption was observed was estimated as the titer of that particular serum.

The results (shown in FIG. 1) indicate that the dilution curve runs almost parallel for native as well as recombinant PSA containing C-terminal $His_{6x}$ suggesting that antibodies raised by recombinant PSA bound to a chitosan-zinc chelate recognized the native PSA as well as the recombinant PSA. Rat sera generated by immunization of rats with native PSA recognized the recombinant PSA in ELISA and the dilution curves were also parallel (data not shown). The purified recombinant PSA containing C-terminal $His_{6x}$ tag was also recognized in a radioimmunoassay system using a PSA IRMA kit (Diagnostic Products Corporation,Los Angeles, Calif.; data not shown).

EXAMPLE 8

Rat Anti-Psa Specificity

In order to characterize the specificity and purity of the antibodies obtained from immunized rats, the rat sera (anti-recombinant PSA antisera) was used in Western immunoblot analysis, performed according to the method of Towbin et al., *Proc. Natl. Acad. Sci. USA* 76:4350–4354 (1979). Specifically, purified human PSA from whole human seminal plasma and CHO expressed recombinant human PSA were run on 4–20% SDS-PAGE gel and blotted to a nitrocellulose membrane. The rat antiserum (containing anti-recombinant PSA antibodies) obtained in Example 7 was then used (at a dilution of 1:5000) in the Western analysis to determine its specificity (see Example 1, for actual methods for western analysis).

Immunoblot results indicate that the rat antisera (containing the anti-recombinant PSA antibodies) recognized a band of similar molecular weight to the purified recombinant PSA as well as the native PSA isolated from human seminal plasma.

EXAMPLE 9

Binding of Rat Anti-Psa Antibodies to Human Prostate Cancer Cells

In order to assess the binding capabilities of the PSA antibodies contained in the rat antisera (see Example 7), the antisera was used in immunofluorescence studies to determine the pattern of localization on human prostate tumor cell lines, Du145 and LnCap., (ATCC HTB81 and ATCC CRL1640; American Type Culture Collection, Manassas, Va.). LnCap and DU145 cells were grown on chamber slides (Nunc) for 48 hr 37° C. in a $CO_2$ incubator. The cells were washed 3 times with Cold HBSS (Hank's Balanced Salt Solution) and were subsequently fixed by treatment with cold (4° C.) 90% ethanol for 5 minutes at room temperature. The fixed cells were then washed (twice) HBSS and immediately incubated with rat anti-recombinant PSA or rat anti-native PSA antisera at a dilution of 1:500. The control cells were incubated with pre-immune sera at 1:500 dilution. The fixed cells were then incubated for 2 hours at 37° C. in a humidified chamber. Following incubation with the antisera, the cells were washed 4 times with HBSS. Rabbit anti-rat IgG FITC conjugate (Zymed, San Francisco, Calif.) was then added to the cells and further incubated for 1 hour at 37° C. Following incubation, the cells were washed with HBSS 3 times and mounted in Aquamount (Zymed, San Francisco, Calif.). The slides were then observed under fluorescence microscope on the epifluorescence setting.

Results indicate that LnCap cells showed a very intense staining of the cell membrane by the anti-PSA antibodies and that staining could also be seen in the cytoplasm. With respect to Du145 cells, the staining appeared to weaker and very diffuse as compared to the staining of the LnCap cells, although the actual staining was distinct and more intense as compared to the controls.

EXAMPLE 10

Effect of Rat Anti-Psa Antisera on the Proliferation of Human Prostate Cells In Vitro In order to assess the effect of PSA antibodies contained in the rat antisera (see Example 7) on the proliferation of human prostatic carcinoma cells, cell lines LnCap and Du145, were plated ($10^4$ per ml) in 96-well tissue culture plates and allowed to grow and attach for 24 hours at 37° C. in a $CO_2$ incubator. Rat anti-recombinant PSA antisera, at various dilutions (final dilutions: 1:10,1:20,1:40) was added to the cells, followed by the addition of 5% guinea pig complement (Colorado Serum Co., Denver, Colo.).

Pre-immune sera served as the control. The cells were allowed to incubate with the antibodies (contained in the antisera) for at least 72 hours. Following incubation with antibodies, $^3$H-thymidine (Amersham, Arlington Heights, Ill.) was added and cells were further incubated for 24 hours. The cells were harvested and the incorporation of $^3$H-thymidine in cells was determined via scintillation counting.

Figure 2:
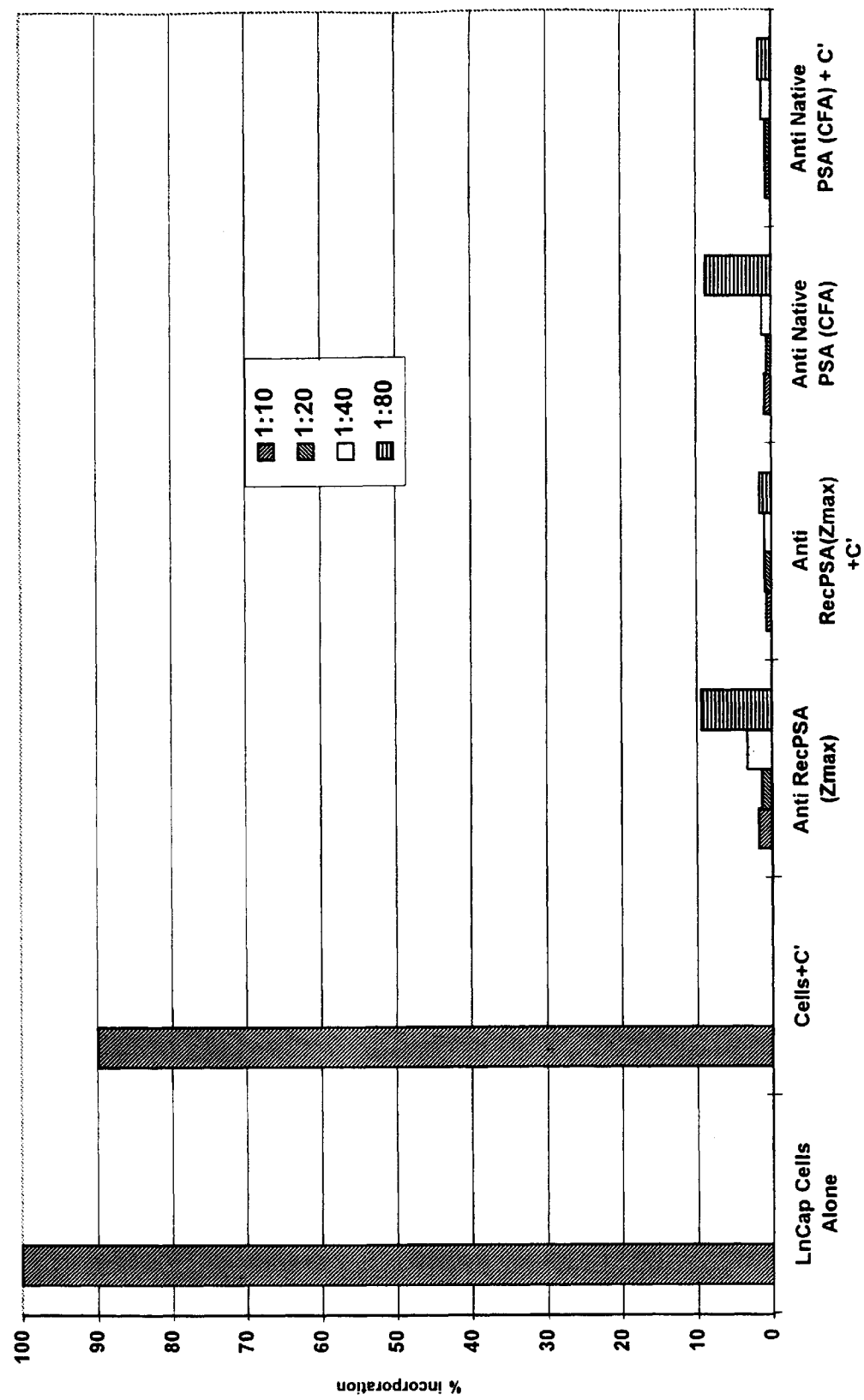
FIGS. 2 and 3 demonstrate the effect of rat anti-recombinant PSA antibodies on prostatic carcinoma cell lines LnCap and Du145, respectively, to incorporate $^3$H-thymidine.
Figure 3:
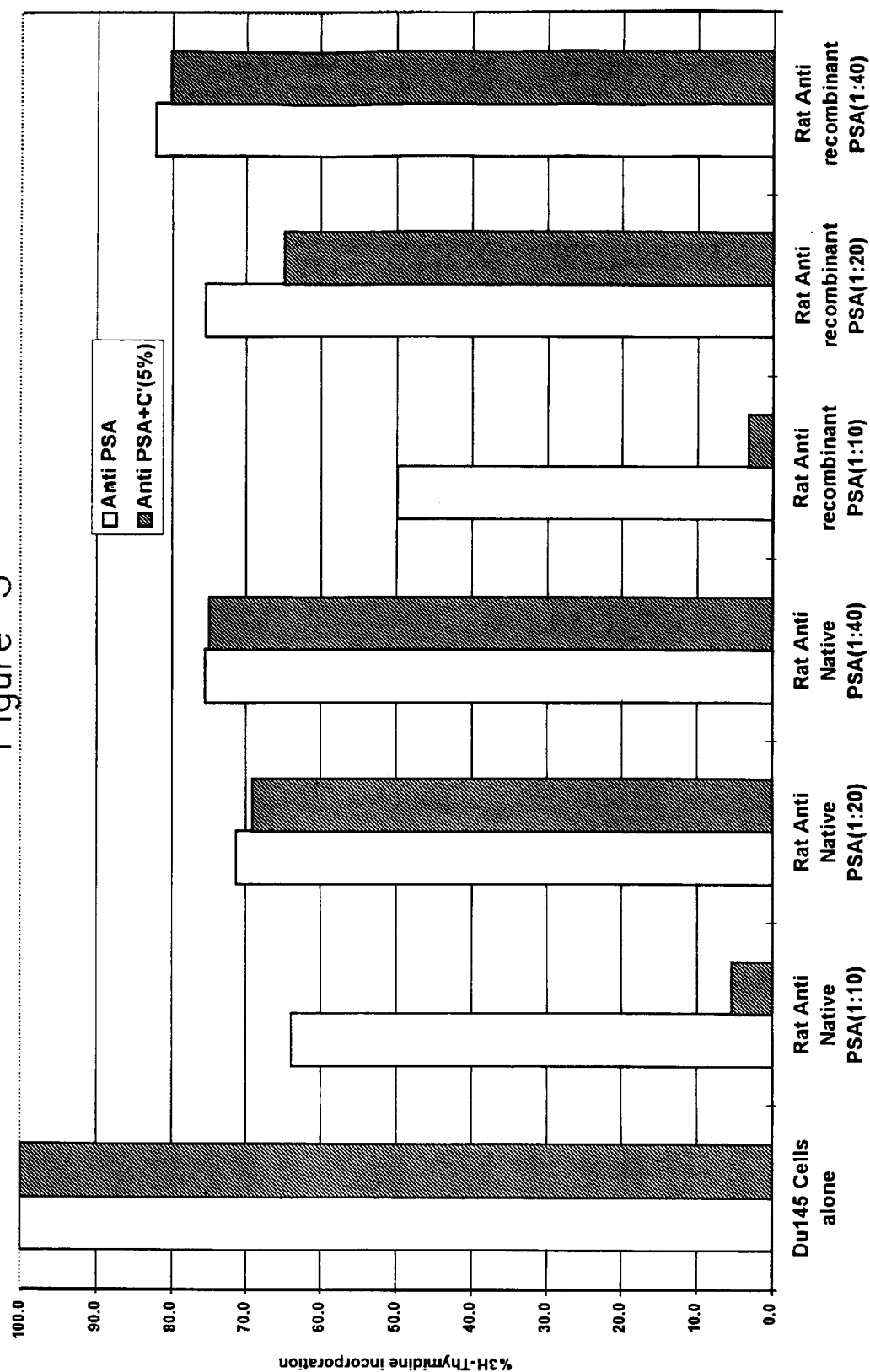

FIGS. 2 and 3 show the results obtained and indicate that the antisera (containing anti-recombinant PSA antibodies) alone were cytotoxic in a dose-dependent manner, as measured by the decreased ability of LnCap cells to incorporate thymidine. This effect was more pronounced when complement was present. However, in the case of Du145 cells, the ability of the cells to uptake thymidine was decreased by about 40% at 1:10 dilution when antisera containing antibodies alone was added, whereas in presence of complement thymidine uptake was reduced by 95%. At higher dilutions (1:20 and 1:40) less cytotoxic effects were observed.

EXAMPLE 11

Immunization and Characterization of the Immune Response in Rhesus Monkeys

Two male rhesus monkeys were immunized with recombinant human PSA/chitosan-zinc chelate prepared as described above. Each animals received 250 μg equivalent of recombinant PSA as PSA/chitosan-zinc chelate once every month for first three months followed by another injection after 6 months, after the titers had started to decline. Two control monkeys received the chitosan-zinc chelate only. Another set of monkeys were immunized with native human PSA/chitosan-oil emulsion (adjuvant of Example 6) isolated from human semen, each receiving 250 μg per animal, once a month for three months, followed by final injection at the 6 months.

Animals were bled every 2 weeks and the serum titers were measured via ELISA (as described in Example 7) against recombinant as well as native PSA. Total serum testosterone was also determined (using a kit purchased from Diagnostic Product Corp., Los Angeles, Calif.) throughout the study period. The monkeys were euthanized after the study and prostate, seminal vesicles and testis were obtained, weighed, and inspected for any gross abnormalities.

Figure 4:
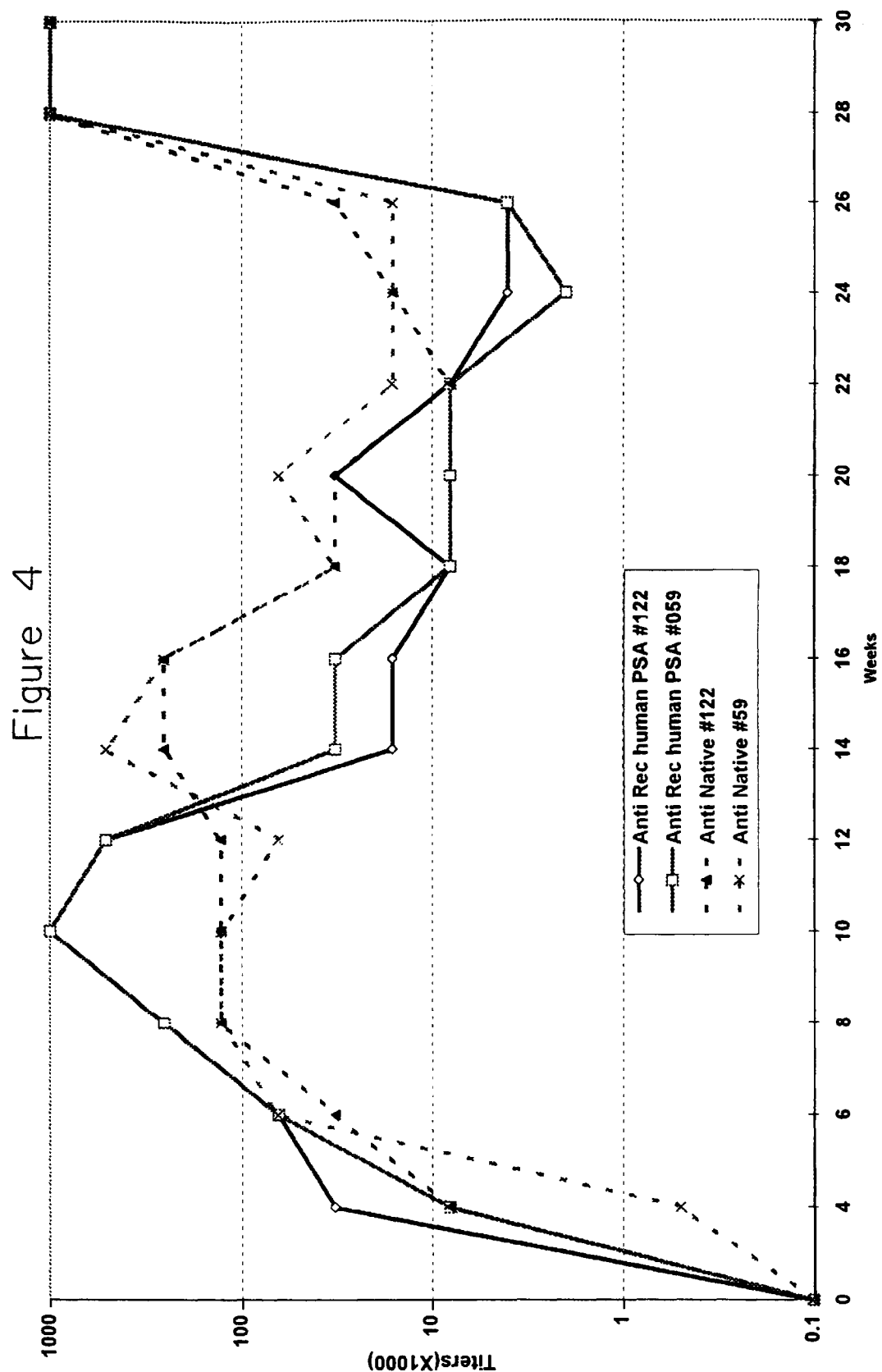
FIG. 4 sets forth the titers in the serum of monkeys to the recombinant PSA/chitosan-zinc chelate as well as native PSA subsequent to immunization.

FIG. 4, shows the antibody titers in the serum of the monkeys against recombinant PSA as well as against native PSA. The titers to natural and recombinant PSA were similar, demonstrating that the recombinant human PSA was able to elicit an immune response not only against the administered antigen (i.e. recombinant PSA) but the antibodies also recognized native PSA as well. The immunotherapeutic agent comprising the recombinant PSA/chitosan-zinc chelate was found to be immunogenic in rhesus, even though human and rhesus monkey PSAs are approximately 89% homologous at the protein level [Gauthier et al. *Biochim Biophys. Acta*, 1174:207–210 (1993)].

Figure 5:
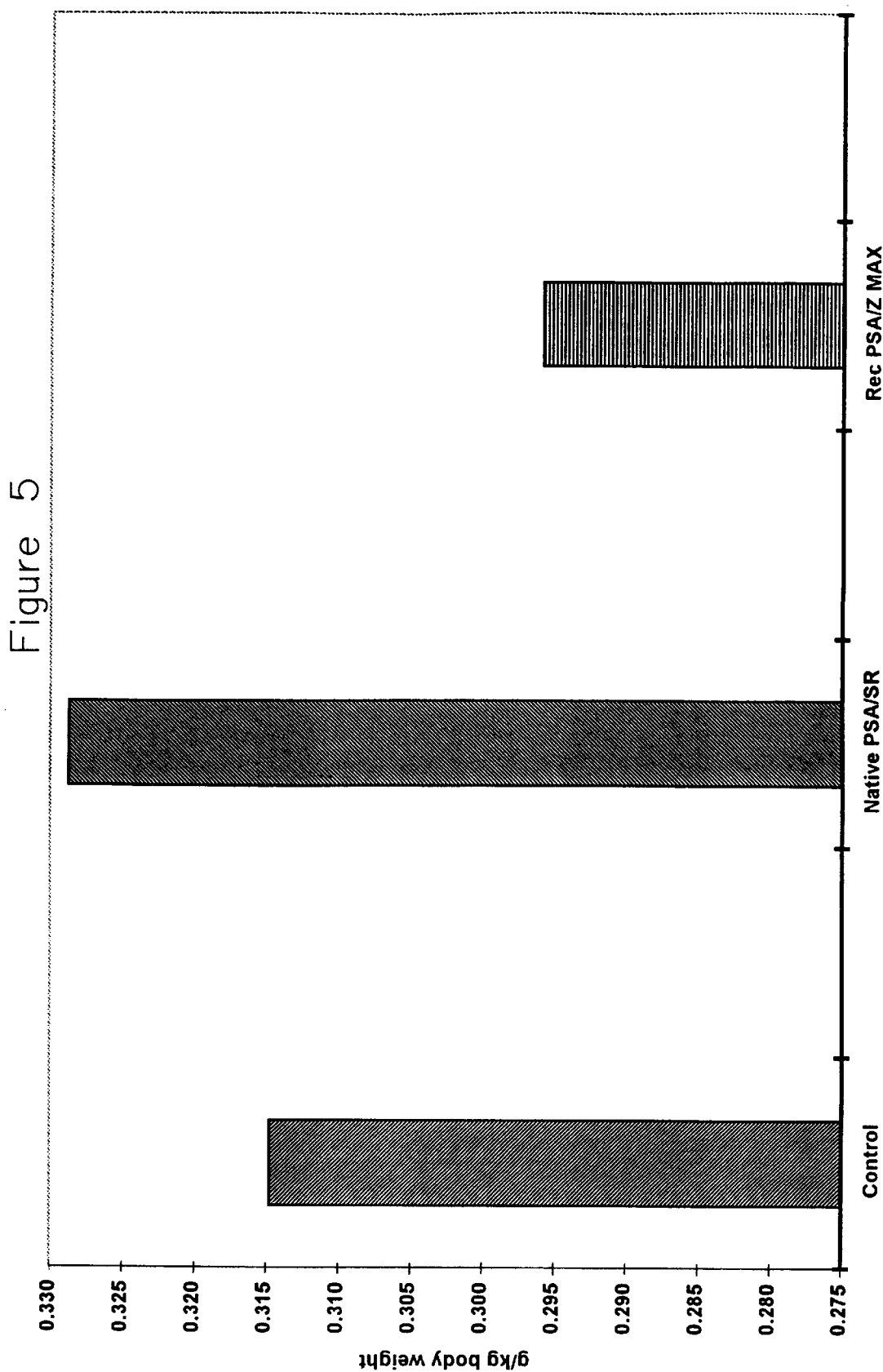
FIG. 5 sets forth the prostate organ weight of the monkeys immunized with either recombinant PSA/chitosan-zinc chelate or native PSA/chitosan-oil emulsion.

No measurable effects were seen with the testosterone levels of the monkeys, with respect to the immunization with PSA. There was a slight reduction in the weight of prostate (see FIG. 5) of the monkeys immunized with the recombinant PSA/chitosan-zinc chelate immunotherapy. The autopsy of these animals did not reveal any gross abnonnalities in the prostate or other reproductive tissue such as seminal vesicles, testis or epidydmis.

EXAMPLE 12

Effect of Monkey Anti-PSA Antisera on In Vitro Proliferation of Human Prostate Cancer Cells Human prostate cell lines, LnCap andeDu145, were plated ($10^4$ per ml) in 96 well tissue culture plates and allowed to attach and grow for 24 hours at 37° C. in a $CO_2$ incubator. Monkey antisera (see Example 14), at various dilutions (final dilutions: 1:10,1:20,1:40), was added to the cells followed by addition of 5% guinea pig complement (Colorado Serum Co., Denver, Colo.). Pre-immune sera served as the control. The cells were allowed to incubate with the antisera containing the anti-recombinant PSA antibodies for at least 72 hours. Following the incubation with the antisera, $^3$H-thymidine (Amersham, Arlington Heights, Ill.) was added and the cells were further incubated for 24 hours. The cells were harvested and the incorporation of $^3$H-thymidine in cells determined by scintillation counting.

Figure 6:
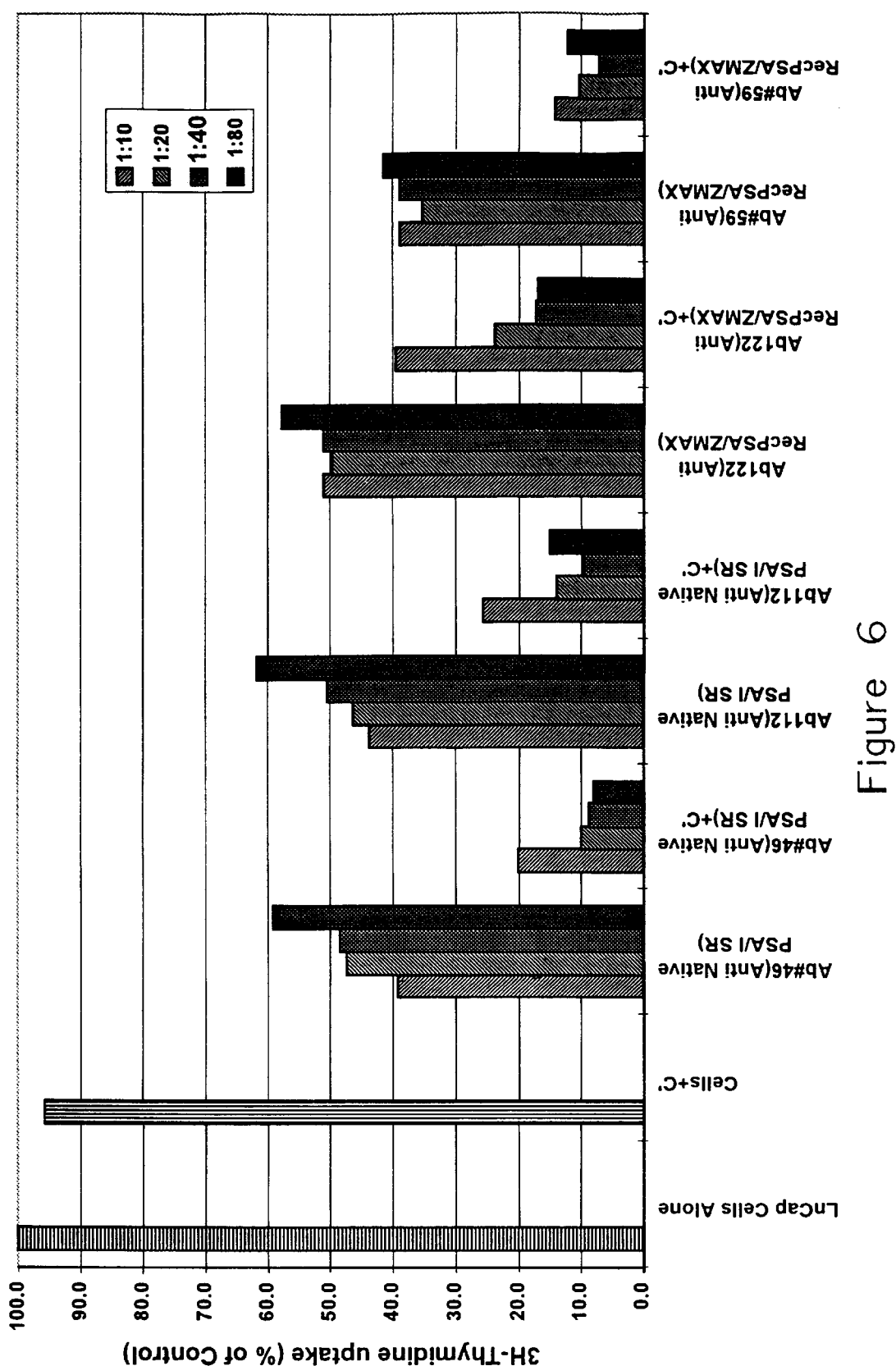
FIG. 6 shows the effect of monkey antisera, from animals immunized with either recombinant PSA/chitosan-zinc chelate or native PSA, on the growth of LnCap prostatic carcinoma cells in the presence and absence of guinea pig complement.
Figure 7:
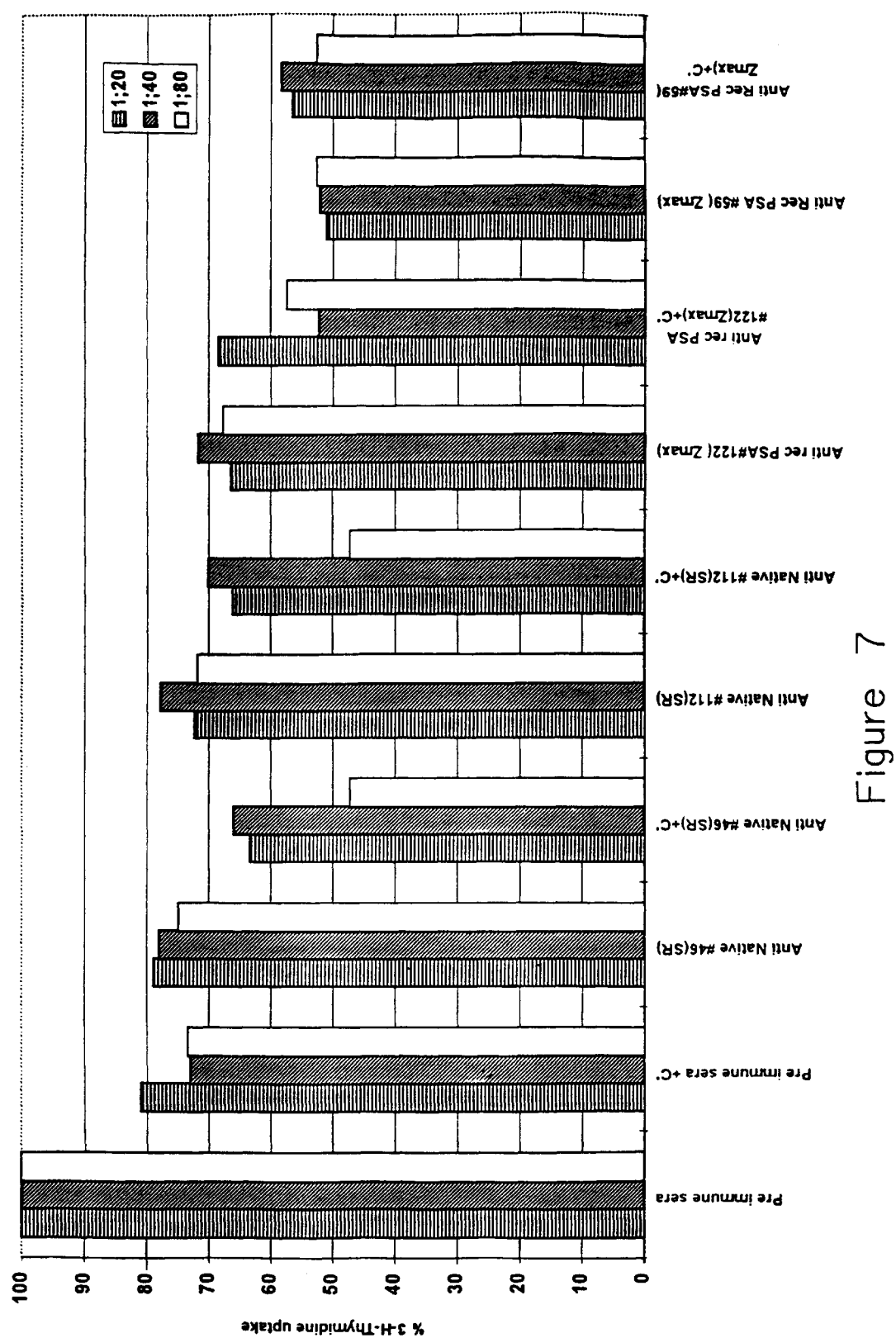
FIG. 7 illustrates the effect of monkey antisera, from animals immunized with either recombinant PSA/chitosan-zinc chelate or native PSA, on the growth of Du145 prostatic carcinoma cells in the presence and absence of guinea pig complement.

Results (FIG. 6) indicate that the monkey antisera alone was effective in inducing cellular cytotoxicity, as noted by the decreased incorporation of thymidine by the LnCap cells. The cytotoxic effect was enhanced in the presence of complement. Results with respect to Du145 cells (see FIG. 7) indicated that the monkey antisera alone was also capable of inducing a cytotoxic effect and also was more effective in presence of complement, though the cytotoxic effect was less than that seen with LnCap cells.

EXAMPLE 13

Effect of Anti-PSA Antibodies on In Vivo Growth of Human Prostate Cancer Cells Du145 prostatic tumor cells ($2.5 \times 10^6$ suspended in 0.1 ml Hanks balanced salt solution) were injected subcutaneously in the shoulder at two sites in the athymic nude mice (20–25 g Harlan, Houston, Tex.). Following the appearance of visible tumors (appeared during Week 2), the mice were injected intraperitoneally with 0.1 ml of partially purified monkey anti-recombinant PSA or anti-native PSA antibodies (having a titer of 1:106) twice a week for 8 weeks.

Partially purified antibodies were prepared by using ammonium sulfate precipitation. Specifically, a 10 ml aliquot of each sera was obtained from the monkeys (receiving either adjuvant alone, recombinant PSA or native PSA) and treated with a saturated solution of ammonium sulfate, pH 7.0. Ammonium sulfate was added drop wise to the serum sample, with continuous vortexing to allow uniform mixing. The mixture was then left overnight at 4° C. After overnight incubation, the sample was centrifuged at 2,000×g and the resulting pellet was resuspended in 2 ml of PBS. The excess of ammonium sulfate was removed by dialyzing against cold PBS with 5 changes of PBS. The protein content was measured by Coomassie Plus Protein Assay Reagent (Pierce, Rockford, Ill.), with the final protein content adjusted to 1 mg/ml with PBS. The final preparation was then sterile filtered. Control animals received adjuvant only, while a third set of animals received a native PSA/chitosan-oil emulsion (adjuvant of Example 6). Tumor diameters were measured twice a week during the 8 week duration. The animals were euthanized after the study and the tumors were excised. Any fluid from the tumors was blotted out and the tumors were weighed. A part of the tumor was fixed in Bouin's fixative.

Figure 8:
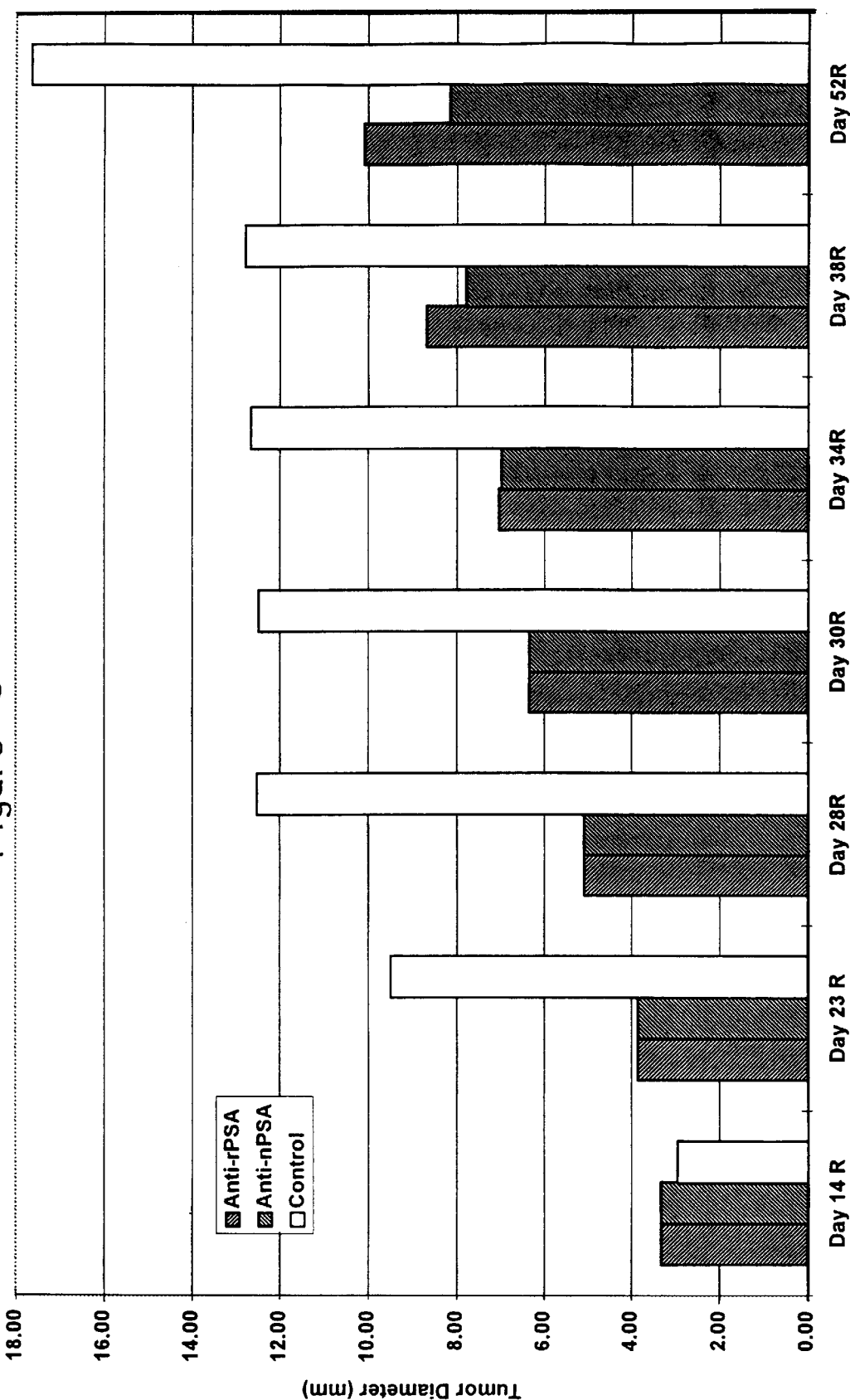
FIG. 8 demonstrates the growth of the tumors in animals receiving adjuvant only versus animals receiving either partially purified anti-recombinant PSA antibodies or partially purified anti-native PSA antibodies in terms of tumor diameter over time.

FIG. 8, which sets forth the results of a passive immunization study, indicates that the tumors in control animals grew faster as compared to the tumors in animals that received partially purified anti-PSA antibodies from monkeys that were immunized with recombinant PSA/chitosan-zinc chelate or that were immunized with the native PSA.

The weights of the tumors from the experimental animals was found to be much lower than that of the control animals (data not shown). The tumors in the experimental group receiving anti recombinant or native PSA antibodies were fluid filled as compared to the solid tumor mass in the control group.

EXAMPLE 14

Effect of Early Antibody Injection on DU145 Tumor incidence in Athymic Mice

This experiment was carried out in a manner similar to Example 13, except that the partially purified monkey anti-recombinant PSA or anti-native PSA antibodies were injected on day 10 following injection of Du145 cells into athymic nude mice. As in Example 13, Du145 cells were injected in nude mice at two sites on the shoulders of the animals. On day 10 following the injection of the cells the mice were divided into three groups of five animals each [as in Example 13, tumors appeared during Week 2]. The mice were injected intraperitoneally with partially purified monkey anti-recombinant PSA or anti-native PSA antibodies twice a week for weeks. The control group received antibodies from monkeys that were injected with adjuvant only. The tumor incidence was monitored during weeks 8–12. The animals were euthanized after the study and the tumors were excised.

Results indicate that during week 12 a single tumor was observed across the five animals that received anti-recombinant PSA antibodies, while in the group of five animals that received anti-native PSA antibodies two tumors were observed. In the control group all five animals developed tumors. These results demonstrate that the PSA/chitosan-zinc chelate was able to induce the production of antibodies, which were shown, by passive immunization studies, to inhibit the growth and incidence of prostate-associated tumors.

To determine the relative immune response against the recombinant PSA, plus or minus the chitosan-zinc chelate adjuvant, preliminary studies have been conducted in mice. Specifically, 4 to 5 male mice (25 g) were immunized (approximately 10 μg of the antigen) with either the recombinant PSA (produced as in Example 1) alone or with the recombinant PSA/chitosan-zinc chelate of the present invention. Animals received a booster injection at day 30 following the initial administration. Initial results demonstrated that animals receiving the PSA alone had serum titers (against the antigen) of less than 1:250, while animals receiving the PSA/chitosan-zinc chelate had titers of greater than 12.8 K, which upon administration of the booster injection reached levels of greater then 512 K. These preliminary results indicate that recombinant PSA alone is not immunogenic, while the PSA/chitosan-zinc chelate composition is highly immunogenic.

EXAMPLE 15

Treatment of Prostate and Prostate-associated Tumors in Humans

In view of the foregoing passive immunization studies wherein antibodies to the immunotherapeutic agent, recombinant PSA/chitosan-zinc chelate, were shown to inhibit the growth and incidence of prostate-associated tumors, this example is directed to the treatment of human prostate-associated tumors (actual tumors of the prostate as well as metastatic tumors of prostatic origin) via the administration of the immunotherapeutic agents set forth above (i.e., a prostate-associated antigen in conjunction with a chitosan-based adjuvant). Although PSA is exemplified below as the prostate-related antigen, those of skill in the art will readily recognize that other prostate-related antigens such as PSMA, HK2, PCTA-1, PTI-1, PSCA, PAP, LH receptor, and PTEN/MMAC1 may be used in the practice of the present invention. Further, while the chitosan-metal chelate adjuvant is exemplified below, those of skill in the art will readily understand that other chitosan-based adjuvants (see Examples 5 and 6) may be used in the practice of the invention.

Specifically, an individual diagnosed with prostate carcinoma or metastatic carcinoma of prostatic origin is administered an immunotherapeutic agent containing recombinant PSA (and/or other prostate associated antigens) chitosan-zinc chelate(produced as set forth in Example 3), in an amount effective to stimulate the individual's own immune system to produce antibodies directed to the prostate associated antigens. The administration may take place by any suitable route of administration, including oral, subcutaneous, and parenteral administration. Examples of parenteral administration include intravenous, intraarterial, intramuscular, and intraperitoneal. Following the initial administration of the therapeutic agent, serum titers against the prostate-associate antigens are monitored over time to determine if booster administrations of the therapeutic agent are required.

Regardless of the manner of administration, the specific dose may be calculated according to such factors as body weight or body surface. Further refinement of the calculations necessary to determine the appropriate dosage for treatment of prostatic carcinoma is routinely made by those of ordinary skill in the art without undue experimentation. Appropriate dosages may be ascertained through use of established assays for determining dosages (i.e., correlating serum titers against the prostate associated antigen with reduction in tumor burden). Based upon data gathered from animals (see above), the amount of antigen (single-dose) for administration to a human ranges from about 1 pg to about 1 mg, and more preferably 1 µg to about 800 µg, although it may vary. After the initial dosing, it is possible that booster doses of the immunotherapeutic agents may be required to obtain optimal anti-tumor effects.

During the course of treatment, effects of the immunotherapeutic agent (i.e., reduction in tumor size and/or reduction in the number of tumors) on neoplasms located in or near the prostate are evaluated by rectal ultrasound or other non-invasive technique. With respect to metastatic neoplasms of prostatic origins, effects of the immunotherapeutic agent are evaluated by use of such techniques as computed-tomography scanning or magnetic resonance imaging, Further, determination of serum levels of prostate-associated antigens are also appropriate to evaluate the effectiveness of the agent.

Although the present invention has been described in terms of preferred embodiments, it is intended that the present invention encompass all modifications and variations that occur to those skilled in the art upon consideration of the disclosure herein, and in particular those embodiments that are within the broadest proper interpretation of the claims and their requirements.

All literature cited herein is incorporated by reference.

What is claimed is:

1. A method of inhibiting the growth or alleviating prostatic carcinoma or metastatic caricnoma of prostatic orgigin, the method comprising the administration of a composition comprising prostate-specific antigen and a chitosan-metal chelate selected from the group consisting of chitosan-zinc chelates, chitosan-copper chelates, chitosan-iron chelates, and chitosan-nickel chelates.

2. The composition according to claim 1, wherein the concentration of metal ranges from about 0.7 mM to about 143 mM.

3. The compostion according to claim 1, wherein the amount of prostate-specific antigen ranges from about 1 pg to about 1 mg.

4. The composition according to claim 1, wherein the amount of prostate-specific antigen ranges from about 1 µg to about 800 µg.

* * * * *